(12) United States Patent
Sheldon et al.

(10) Patent No.: US 12,370,371 B2
(45) Date of Patent: Jul. 29, 2025

(54) RATE SMOOTHING IN ATRIAL SYNCHRONOUS VENTRICULAR PACEMAKER

(71) Applicant: MEDTRONIC, INC., Minneapolis, MN (US)

(72) Inventors: Todd J. Sheldon, North Oaks, MN (US); Keelia M. Escalante, Minneapolis, MN (US); Yanina Grinberg, Plymouth, MN (US); Aaron M. Saikin, Round Lake, IL (US)

(73) Assignee: Medtronic, Inc., Minneapolis, MN (US)

( * ) Notice: Subject to any disclaimer, the term of this patent is extended or adjusted under 35 U.S.C. 154(b) by 526 days.

(21) Appl. No.: 17/697,795

(22) Filed: Mar. 17, 2022

(65) Prior Publication Data

US 2022/0323768 A1    Oct. 13, 2022

Related U.S. Application Data

(60) Provisional application No. 63/173,523, filed on Apr. 12, 2021.

(51) Int. Cl.
*A61N 1/365* (2006.01)
*A61N 1/372* (2006.01)

(52) U.S. Cl.
CPC ..... *A61N 1/36542* (2013.01); *A61N 1/36521* (2013.01); *A61N 1/36564* (2013.01); *A61N 1/36578* (2013.01); *A61N 1/37211* (2013.01)

(58) Field of Classification Search
CPC ............................. A61N 1/3627; A61N 1/3682
See application file for complete search history.

(56) References Cited

U.S. PATENT DOCUMENTS

| 4,485,813 | A | 12/1984 | Anderson et al. |
| 5,052,388 | A | 10/1991 | Sivula et al. |
| 5,480,413 | A | 1/1996 | Greenhut et al. |
| 5,507,782 | A | 4/1996 | Kieval et al. |
| 5,593,431 | A | 1/1997 | Sheldon |

(Continued)

FOREIGN PATENT DOCUMENTS

| WO | 2018102639 A1 | 6/2018 |
| WO | 2019010353 A1 | 1/2019 |
| WO | 20190204682 A1 | 10/2019 |

OTHER PUBLICATIONS

Cooper, et al., "Absent Ventricular Tachycardia Detection in a Biventricular Implantable Cardioverter-Defibrillator due to Intradevice Interaction with a Rate Smoothing Pacing Algorithm", Heart Rhythm Society, vol. 1, No. 6, Dec. 1, 2004, 4 pages.

(Continued)

*Primary Examiner* — George R Evanisko

(57) ABSTRACT

A medical device is configured to determine a rate smoothing pacing interval based on at a ventricular cycle length ending with a ventricular pacing pulse and determine a post-sense ventricular pacing interval based on a ventricular cycle length ending with a sensed ventricular event signal. The medical device may be configured to start a ventricular pacing interval set to the post-sense ventricular pacing interval in response to the sensed ventricular event signal and generate a ventricular pacing pulse in response to the expiration of the post-sense ventricular pacing interval.

19 Claims, 9 Drawing Sheets

(56) References Cited

U.S. PATENT DOCUMENTS

| | | |
|---|---|---|
| 5,792,193 A | 8/1998 | Stoop |
| 5,885,471 A | 3/1999 | Ruben et al. |
| 5,893,882 A | 4/1999 | Peterson et al. |
| 6,044,297 A | 3/2000 | Sheldon et al. |
| 6,434,424 B1 | 8/2002 | Igel et al. |
| 6,501,987 B1 | 12/2002 | Lovett et al. |
| 6,904,315 B2 | 6/2005 | Panken et al. |
| 7,181,278 B2 * | 2/2007 | Kramer ............... A61N 1/3627 607/9 |
| 7,502,646 B2 | 3/2009 | Sheldon et al. |
| 7,532,929 B2 | 5/2009 | Mussig et al. |
| 7,894,898 B2 | 2/2011 | Sheldon et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 9,675,798 B2 | 6/2017 | Grubac et al. |
| 9,808,633 B2 | 11/2017 | Bonner et al. |
| 10,207,116 B2 | 2/2019 | Sheldon et al. |
| 10,286,214 B2 | 5/2019 | Demmer et al. |
| 10,328,270 B2 | 6/2019 | Demmer et al. |
| 10,449,366 B2 | 10/2019 | Splett et al. |
| 10,532,212 B2 | 1/2020 | Splett et al. |
| 2016/0129263 A1 | 5/2016 | Demmer et al. |
| 2016/0144190 A1 | 5/2016 | Cao et al. |
| 2017/0368347 A1 | 12/2017 | Muessig et al. |
| 2017/0368360 A1 | 12/2017 | Hahn et al. |
| 2019/0009095 A1 | 1/2019 | Sheldon et al. |
| 2019/0083800 A1 | 3/2019 | Yang et al. |
| 2019/0321634 A1 * | 10/2019 | Sheldon ............. A61N 1/36507 |

OTHER PUBLICATIONS (PCT/US2019/028234) PCT Notification of Transmittal of the International Search Report and the Written Opinion of the International Searching Authority, Mailed Jul. 10, 2019, 13 pages.

Halawa, et al., Syncope after successful implantation of atrioventricular synchronous leadless pacemaker caused by polymorphic ventricular tachycardia, Published in Heart Rhythm Society, Case Report, vol. 6, Issue 8, on May 18, 2020, 4 pages.

European Search Report Completed Sep. 7, 2022, European Patent Application No. 22167686.9, 8 pages.

* cited by examiner

RATE SMOOTHING IN ATRIAL SYNCHRONOUS VENTRICULAR PACEMAKER

REFERENCE TO RELATED APPLICATIONS

This application claims the benefit of provisional U.S. Patent Application No. 63/173,523, filed on Apr. 12, 2021, incorporated herein by reference in its entirety.

TECHNICAL FIELD

This disclosure relates to a ventricular pacemaker and a method for controlling ventricular pacing pulse intervals for promoting atrial synchronous ventricular pacing.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two transvenous, intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some heart rhythm conditions, some patients may benefit from atrial and ventricular (dual chamber) sensing for providing atrial-synchronized ventricular pacing in order to maintain a more normal heart rhythm.

SUMMARY

The techniques of this disclosure generally relate to controlling a ventricular pacing interval for scheduling delivery of ventricular pacing pulses generated by a medical device to avoid abrupt changes in ventricular rate and promote atrial event sensing for enabling atrial synchronized ventricular pacing. The medical device may be ventricular pacemaker, such as an intracardiac ventricular pacemaker, configured to sense atrial systolic events. The medical device may generate ventricular pacing pulses synchronized to the sensed atrial systolic events at an atrioventricular (AV) pacing interval. A medical device configured to perform the techniques disclosed herein determines a rate smoothing pacing interval based on at least one paced ventricular cycle length and determines a post-sense pacing interval based on at least one sensed ventricular cycle length. The medical device may set a ventricular pacing interval, also referred to herein as a "VV pacing interval," to the post-sense pacing interval in response to sensing a ventricular event signal, e.g., an R-wave signal. The medical device may set the VV pacing interval to the rate smoothing interval in response to generating a ventricular pacing pulse. When the VV pacing interval expires without sensing an atrial systolic event, the medical device generates a ventricular pacing pulse at the respective post-sense pacing interval or the rate smoothing interval.

In some examples, the medical device may be configured to determine the rate smoothing interval by determining a first pacing interval based on at least one paced ventricular cycle length according to one method and determining a second pacing interval based on at least one paced ventricular cycle length according to a second method, different than the first method. The medical device may be configured to determine when rate smoothing criteria are met and set the VV pacing interval to the first pacing interval in response to a generated ventricular pacing pulse when the rate smoothing criteria are met. The medical device may set the VV pacing interval to the second pacing interval in response to a generated ventricular pacing pulse when the rate smoothing criteria are unmet.

In one example, the disclosure provides a medical device including a pulse generator configured to generate ventricular pacing pulses, a cardiac electrical signal sensing circuit configured to sense ventricular event signals, and a control circuit. The control circuit is configured to determine a first ventricular cycle length ending with a ventricular pacing pulse generated by the pulse generator, determine a rate smoothing pacing interval based on at least the first ventricular cycle length, determine a second ventricular cycle length ending with a ventricular event signal sensed by the cardiac electrical signal sensing circuit, and determine a post-sense ventricular pacing interval based on the second ventricular cycle length. The control circuit may be configured to start a ventricular pacing interval set to the post-sense ventricular pacing in response to the ventricular event signal sensed by the cardiac electrical signal sensing circuit and determine that the post-sense ventricular pacing interval expires. The pulse generator is configured to generate a ventricular pacing pulse in response to the expiration of the post-sense ventricular pacing interval. The control circuit may be further configured to start the ventricular pacing interval set to the rate smoothing pacing interval in response to the pulse generator generating the ventricular pacing pulse at the expiration of the post-sense ventricular pacing interval.

In another example, the disclosure provides a method including generating a ventricular pacing pulse, determining a first ventricular cycle length ending with the ventricular pacing pulse, determining a rate smoothing pacing interval based on at least the first ventricular cycle length, sensing a ventricular event signal from a cardiac electrical signal, determining a second ventricular cycle length ending with the sensed ventricular event signal, and determining a post-sense ventricular pacing interval based on the second ventricular cycle length. The method may include starting a ventricular pacing interval set to the post-sense ventricular pacing interval in response to the sensed ventricular event signal. The method includes determining that the post-sense ventricular pacing interval expires and generating a ventricular pacing pulse in response to the expiration of the post-sense ventricular pacing interval. The method includes starting the ventricular pacing interval set to the rate smoothing pacing interval in response to the ventricular pacing pulse generated at the expiration of the post-sense ventricular pacing interval.

In yet another example, the disclosure provides a non-transitory, computer-readable storage medium comprising a set of instructions which, when executed by a control circuit of a medical device, cause the medical device to generate a ventricular pacing pulse, determine a first ventricular cycle length ending with the ventricular pacing pulse, determine a rate smoothing pacing interval based on at least the first ventricular cycle length, sense a ventricular event signal from a cardiac electrical signal, determine a second ventricular cycle length ending with the sensed ventricular event signal, and determine a post-sense ventricular pacing interval based on the second ventricular cycle length. The instructions may further cause the device to start a ventricular pacing interval set to the post-sense ventricular pacing interval in response to the sensed ventricular event signal, determine that the post-sense ventricular pacing interval expires, and generate a ventricular pacing pulse in response to the expiration of the post-sense ventricular pacing interval. The instructions may further cause the device to start the ventricular pacing interval set to the rate smoothing pacing interval in response to the ventricular pacing pulse generated at the expiration of the post-sense ventricular pacing interval.

Further disclosed herein is the subject matter of the following clauses:

1. A pacemaker comprising:
    a pulse generator configured to generate ventricular pacing pulses;
    a cardiac electrical signal sensing circuit configured to sense ventricular event signals;
    a control circuit configured to:
    determine a first ventricular cycle length ending with a first ventricular pacing pulse generated by the pulse generator;
    determine a rate smoothing pacing interval based on at least the first ventricular cycle length;
    determine a second ventricular cycle length ending with a ventricular event signal sensed by the cardiac electrical signal sensing circuit;
    determine a post-sense ventricular pacing interval based on the second ventricular cycle length;
    start a ventricular pacing interval set to the post-sense ventricular pacing interval in response to the ventricular event signal sensed by the cardiac electrical signal sensing circuit; and
    determine that the post-sense ventricular pacing interval expires;
    wherein the pulse generator is configured to generate a second ventricular pacing pulse in response to the expiration of the post-sense ventricular pacing interval; and
    the control circuit is configured to start the ventricular pacing interval set to the rate smoothing pacing interval in response to the pulse generator generating the second ventricular pacing pulse at the expiration of the post-sense ventricular pacing interval.
2. The medical device of clause 1,
    wherein the control circuit is further configured to:
    receive an atrial event signal;
    set an atrioventricular pacing interval in response to the received atrial event signal; and
    determine that the atrioventricular pacing interval expires;
    wherein the pulse generator is configured to generate the first ventricular pacing pulse in response to the atrioventricular pacing interval expiring; and
    wherein the control circuit is configured to determine the first ventricular cycle length ending with the first ventricular pacing pulse generated in response to the atrioventricular pacing interval expiring.
3. The medical device of clause 2, further comprising a sensor configured to sense a cardiac signal; wherein the control circuit is configured to receive the atrial event signal by receiving the cardiac signal from the sensor and sensing the atrial event signal from the cardiac signal.
4. The medical device of clause 3, wherein the sensor comprises any of: an electrode, an accelerometer, an impedance sensor, an acoustical sensor and a pressure sensor.
5. The medical device of clause 2, further comprising a communication circuit, wherein the control circuit is configured to receive, via the communication circuit, the atrial event signal transmitted from another medical device.
6. The medical device of clause 1, further comprising:
    a sensor configured to sense a cardiac signal;
    wherein the control circuit is further configured to:
    sense an atrial event from the cardiac signal;
    set an atrioventricular pacing interval in response to the sensed atrial event; and
    determine that the atrioventricular pacing interval expires;
    wherein the pulse generator is configured to generate the first ventricular pacing pulse in response to the atrioventricular pacing interval expiring; and
    wherein the control circuit is configured to determine the first ventricular cycle length ending with the first ventricular pacing pulse generated in response to the atrioventricular pacing interval expiring.
7. The medical device of clause 6, wherein the sensor comprises an accelerometer configured to produce an acceleration signal.
8. The medical device of clause 6, wherein the sensor comprises any of: an electrode, an impedance sensor and a pressure sensor.
9. The medical device of any of clauses 1-8, wherein the control circuit is further configured to determine the post-sense ventricular pacing interval based on the second ventricular cycle length by determining a greater one of the second ventricular cycle length plus an increment and a predetermined minimum post-sense ventricular pacing interval.
10. The medical device of clause 9, wherein the control circuit is further configured to determine the post-sense ventricular pacing interval by:
    determining that the second ventricular cycle length plus the increment is greater than a maximum limit; and
    determining the post-sense ventricular pacing interval to be the maximum limit in response to the second ventricular cycle length plus the increment being greater than the maximum limit.
11. The medical device of any of clauses 1-10, wherein the control circuit is further configured to:
    update the first ventricular cycle length in response to each ventricular pacing pulse that is generated by the pulse generator at an expiration of one of an atrioventricular pacing interval or the rate smoothing interval;
    update the rate smoothing pacing interval in response to the updated first ventricular cycle length; and
    withhold updating the rate smoothing pacing interval in response to the second ventricular pacing pulse generated by the pulse generator at the expiration of the post-sense ventricular pacing interval.

12. The medical device of any of clauses 1-11, wherein the control circuit is further configured to set the ventricular pacing interval to the rate smoothing pacing interval by:
determining a first pacing interval based on at least the first ventricular cycle length according to a first method;
determining a second pacing interval based on the first ventricular cycle length according to a second method different than the first method;
determining when rate smoothing criteria are met;
setting the ventricular pacing interval to the first pacing interval in response to the rate smoothing criteria being met; and
setting the ventricular pacing interval to the second pacing interval in response to the rate smoothing criteria not being met.
13. The medical device of clause 12, wherein the control circuit is configured to determine that the rate smoothing criteria are met by:
determining a ventricular cycle length metric from a plurality of preceding ventricular cycle lengths; and
determining that the first pacing interval is greater than the ventricular cycle length metric.
14. The medical device of any of clauses 12-13, wherein the control circuit is further configured to:
reset the rate smoothing interval to an initial value; and
determine that the rate smoothing criteria are met by determining that at least a threshold number of ventricular cycles have occurred since resetting the rate smoothing interval.
15. The medical device of any of clauses 12-14, further comprising a sensor for sensing a cardiac signal,
wherein the control circuit is further configured to:
sense atrial events from the cardiac signal; and
determine that the rate smoothing criteria are met by determining that atrial tracking criteria are met based on at least a threshold number of atrial events being sensed from the cardiac signal.
16. The medical device of any of clauses 12-15, wherein the control circuit is further configured to determine that the rate smoothing criteria are met by determining that a plurality of ventricular cycle lengths meet rate stability criteria.
17. The medical device of any of clauses 1-16, further comprising:
a sensor sensing a cardiac signal;
wherein the control circuit is further configured to:
sense an atrial event from the cardiac signal;
determine that the atrial event is sensed after a threshold time interval following a preceding ventricular event; and
determine that the rate smoothing criteria are met in response to determining that the atrial event is sensed after the threshold time interval.
18. A method comprising:
generating a first ventricular pacing pulse;
determining a first ventricular cycle length ending with the first ventricular pacing pulse;
determining a rate smoothing pacing interval based on at least the first ventricular cycle length;
sensing a ventricular event signal from a cardiac electrical signal;
determining a second ventricular cycle length ending with the sensed ventricular event signal;
determining a post-sense ventricular pacing interval based on the second ventricular cycle length;
starting a ventricular pacing interval set to the post-sense ventricular pacing interval in response to the sensed ventricular event signal;
determining that the post-sense ventricular pacing interval expires;
generating a second ventricular pacing pulse in response to the expiration of the post-sense ventricular pacing interval; and
starting the ventricular pacing interval set to the rate smoothing pacing interval in response to the second ventricular pacing pulse generated at the expiration of the post-sense ventricular pacing interval.
19. The method of clause 18, further comprising:
receiving an atrial event signal;
setting an atrioventricular pacing interval in response to receiving the atrial event signal;
determining that the atrioventricular pacing interval expires;
generating the first ventricular pacing pulse in response to the atrioventricular pacing interval expiring; and
determining the first ventricular cycle length ending with the first ventricular pacing pulse generated in response to the atrioventricular pacing interval expiring.
20. The method of clause 19, wherein receiving the atrial event signal comprises sensing a cardiac signal by a sensor and sensing the atrial event signal from the cardiac signal.
21. The method of clause 20, wherein sensing the cardiac signal comprises sensing any of a cardiac electrical signal, an acceleration signal, an acoustical signal, an impedance signal and a pressure signal.
22. The method of clause 19, wherein receiving the atrial event signal comprises receiving the atrial event signal transmitted from another medical device.
23. The method of clause 18, further comprising:
sensing an atrial event from a cardiac signal;
setting an atrioventricular pacing interval in response to sensing the atrial event;
determining that the atrioventricular pacing interval expires;
generating the first ventricular pacing pulse in response to the atrioventricular pacing interval expiring; and
determining the first ventricular cycle length ending with the first ventricular pacing pulse generated in response to the atrioventricular pacing interval expiring.
24. The method of clause 23, wherein sensing the atrial event from the cardiac signal comprises sensing the atrial event from an acceleration signal produced by an accelerometer.
25. The method of clause 23, wherein sensing the atrial event from the cardiac signal comprises sensing the atrial event from any of a cardiac electrical signal, an impedance signal and a pressure signal.
26. The method of any of clauses 18-25, wherein determining the post-sense ventricular pacing interval based on the second ventricular cycle length comprises determining a greater one of the second ventricular cycle length plus an increment and a predetermined minimum post-sense ventricular pacing interval.
27. The method of clause 26, wherein determining the post-sense ventricular pacing interval further comprises:
determining that the second ventricular cycle length plus the increment is greater than a maximum limit; and determining the post-sense ventricular pacing interval to be the maximum limit in response to the second ventricular cycle length plus the increment being greater than the maximum limit.

28. The method of any of clauses 18-27, further comprising:
updating the first ventricular cycle length in response to each ventricular pacing pulse that is generated at an expiration of one of an atrioventricular pacing interval or the rate smoothing interval;
updating the rate smoothing pacing interval in response to the updated first ventricular cycle length; and
withholding updating the rate smoothing pacing interval in response to the second ventricular pacing pulse generated at the expiration of the post-sense ventricular pacing interval.

29. The method of any of clauses 18-28, wherein setting the ventricular pacing interval to the rate smoothing pacing interval comprises:
determining a first pacing interval based on at least the first ventricular cycle length according to a first method;
determining a second pacing interval based on the first ventricular cycle length according to a second method different than the first method;
determining when rate smoothing criteria are met;
setting the ventricular pacing interval to the first pacing interval in response to the rate smoothing criteria being met; and
setting the ventricular pacing interval to the second pacing interval in response to the rate smoothing criteria not being met.

30. The method of clause 29, wherein determining that the rate smoothing criteria are met comprises:
determining a ventricular cycle length metric from a plurality of preceding ventricular cycle lengths; and
determining that the first pacing interval is greater than the ventricular cycle length metric.

31. The method of any of clauses 29-30, further comprising:
resetting the rate smoothing interval to an initial value; and
determining that the rate smoothing criteria are met by determining that at least a threshold number of ventricular cycles have occurred since resetting the rate smoothing interval.

32. The method of any of clauses 29-31, further comprising sensing atrial events from a cardiac signal;
wherein determining that the rate smoothing criteria are met comprises determining that atrial tracking criteria are met based on at least a threshold number of atrial events being sensed from the cardiac signal.

33. The method of any of clauses 29-32, wherein determining that the rate smoothing criteria are met comprises determining that a plurality of ventricular cycle lengths meet rate stability criteria.

34. The method of any of clauses 29-33, further comprising:
sensing an atrial event from a cardiac signal;
determining that the atrial event is sensed after a threshold time interval following a preceding ventricular event; and
determining that the rate smoothing criteria are met in response to the atrial event being sensed after the threshold time interval.

35. A non-transitory, computer-readable storage medium comprising a set of instructions which, when executed by a control circuit of a medical device, cause the medical device to:
generate a first ventricular pacing pulse;
determine a first ventricular cycle length ending with the first ventricular pacing pulse;
determine a rate smoothing pacing interval based on at least the first ventricular cycle length;
sense a ventricular event signal from a cardiac electrical signal;
determine a second ventricular cycle length ending with the sensed ventricular event signal;
determine a post-sense ventricular pacing interval based on the second ventricular cycle length;
start a ventricular pacing interval set to the post-sense ventricular pacing interval in response to the sensed ventricular event signal;
determine that the post-sense ventricular pacing interval expires;
generate a second ventricular pacing pulse in response to the expiration of the post-sense ventricular pacing interval; and
start the ventricular pacing interval set to the rate smoothing pacing interval in response to the second ventricular pacing pulse generated at the expiration of the post-sense ventricular pacing interval.

36. The non-transitory, computer-readable storage medium of clause 35 further comprising instructions that cause the medical device to:
receive an atrial event signal;
set an atrioventricular pacing interval in response to receiving the atrial event signal;
determine that the atrioventricular pacing interval expires;
generate the first ventricular pacing pulse in response to the atrioventricular pacing interval expiring; and
determine the first ventricular cycle length ending with the first ventricular pacing pulse generated in response to the atrioventricular pacing interval expiring.

37. The non-transitory, computer-readable storage medium of clause 36 further comprising instructions that cause the medical device to receive the atrial event signal by:
sensing a cardiac signal by a sensor; and
sensing the atrial event signal from the cardiac signal.

38. The non-transitory, computer-readable storage medium of clause 37 further comprising instructions that cause the medical device to sense the cardiac signal by sensing any of a cardiac electrical signal, an acceleration signal, an acoustical signal, an impedance signal and a pressure signal.

39. The non-transitory, computer-readable storage medium of clause 36 further comprising instructions that cause the medical device to receive the atrial event signal by receiving the atrial event signal transmitted from another medical device.

40. The non-transitory, computer-readable storage medium of any of clauses 35-39 further comprising instructions that cause the medical device to determine the post-sense ventricular pacing interval based on the second ventricular cycle length by determining a greater one of the second ventricular cycle length plus an increment and a predetermined minimum post-sense ventricular pacing interval.

41. The non-transitory, computer-readable storage medium of any of clauses 35-40 further comprising instructions that cause the medical device to determine the post-sense ventricular pacing interval by:
determining that the second ventricular cycle length plus the increment is greater than a maximum limit; and
determining the post-sense ventricular pacing interval to be the maximum limit in response to the second ventricular cycle length plus the increment being greater than the maximum limit.

42. The non-transitory, computer-readable storage medium of any of clauses 35-41 further comprising instructions that cause the medical device to:
update the first ventricular cycle length in response to each ventricular pacing pulse that is generated at an expiration of one of an atrioventricular pacing interval or the rate smoothing interval;
update the rate smoothing pacing interval in response to the updated first ventricular cycle length; and
withhold updating the rate smoothing pacing interval in response to the second ventricular pacing pulse generated at the expiration of the post-sense ventricular pacing interval.

43. The non-transitory, computer-readable storage medium of any of clauses 35-42 further comprising instructions that cause the medical device to set the ventricular pacing interval to the rate smoothing pacing interval by:
determining a first pacing interval based on at least the first ventricular cycle length according to a first method;
determining a second pacing interval based on the first ventricular cycle length according to a second method different than the first method;
determining when rate smoothing criteria are met;
setting the ventricular pacing interval to the first pacing interval in response to the rate smoothing criteria being met; and
setting the ventricular pacing interval to the second pacing interval in response to the rate smoothing criteria not being met.

44. The non-transitory, computer-readable storage medium of clause 43 further comprising instructions that cause the medical device to determine that the rate smoothing criteria are met by:
determining a ventricular cycle length metric from a plurality of preceding ventricular cycle lengths; and
determining that the first pacing interval is greater than the ventricular cycle length metric.

45. The non-transitory, computer-readable storage medium of any of clauses 43-44 further comprising instructions that cause the medical device to:
reset the rate smoothing interval to an initial value; and
determine that the rate smoothing criteria are met by determining that at least a threshold number of ventricular cycles have occurred since resetting the rate smoothing interval.

46. The non-transitory, computer-readable storage medium of any of clauses 43-45 further comprising instructions that cause the medical device to:
sense atrial events from a cardiac signal; and
determine that the rate smoothing criteria are met by determining that atrial tracking criteria are met based on at least a threshold number of atrial events being sensed from the cardiac signal.

47. The non-transitory, computer-readable storage medium of any of clauses 43-46 further comprising instructions that cause the medical device to determine that the rate smoothing criteria are met by determining that a plurality of ventricular cycle lengths meet rate stability criteria.

48. The non-transitory, computer-readable storage medium of any of clauses 43-47 further comprising instructions that cause the medical device to:
sense an atrial event from a cardiac signal;
determine that the atrial event is sensed after a threshold time interval following a preceding ventricular event; and
determine that the rate smoothing criteria are met in response to the atrial event being sensed after the threshold time interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
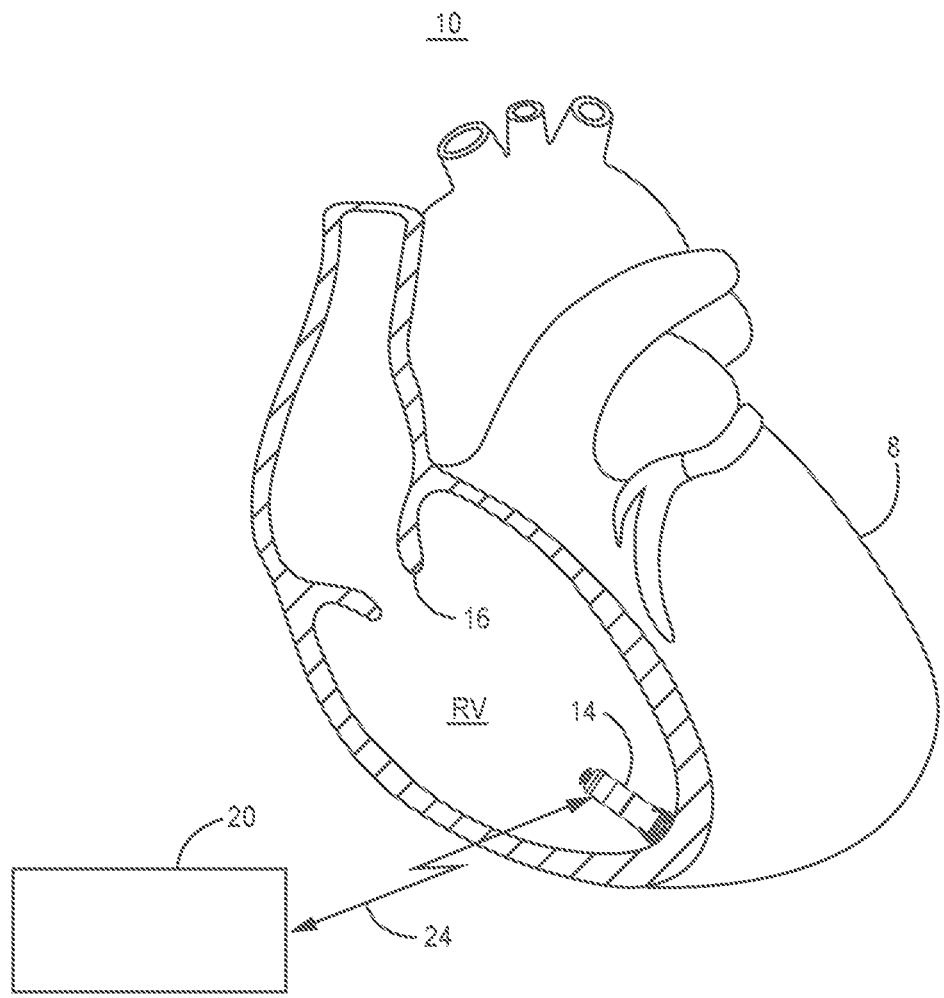
FIG. 1 is a conceptual diagram illustrating a medical device system that may be used to sense cardiac signals and provide ventricular pacing therapy to a patient's heart.

In general, this disclosure describes techniques for controlling ventricular pacing intervals to avoid an abrupt change in ventricular rate and promote atrial synchronous ventricular pacing. In the illustrative examples presented herein, a ventricular pacemaker is configured to sense atrial systolic events for synchronizing the ventricular pacing pulses to the atrial rate. As described below, the atrial systolic events may be sensed from a signal produced by a motion sensor that includes an atrial systolic event signal corresponding to atrial mechanical contraction and the active filling phase of the ventricle, sometimes referred to as the "atrial kick." In other examples, atrial systolic event sensing may be performed using other techniques, such as sensing the atrial systolic event from another cardiac mechanical signal (e.g., a pressure signal, acoustical signal, impedance signal, etc.) or sensing the P-wave of a cardiac electrical signal that is attendant to atrial depolarization.

The techniques disclosed herein provide ventricular rate control by setting a ventricular pacing interval in response to a delivered ventricular pacing pulse according to a rate smoothing interval (RSI) and by setting a ventricular pacing interval in response to a ventricular sensed event according to a post-sense ventricular pacing interval. In the absence of an atrial event sensed during the ventricular pacing interval, the pacemaker delivers a ventricular pacing pulse upon expiration of the RSI or the post-sense ventricular pacing interval.

By controlling the ventricular pacing pulse delivery according to an RSI, the ventricular pacing pulse is less likely to interfere with sensing of the next atrial event, increasing the likelihood of an atrial synchronized ventricular pacing pulse on the next cardiac cycle. By controlling the ventricular pacing pulse delivery according to a post-sense ventricular pacing interval, a long post-sense ventricular interval is avoided. When a ventricular event is sensed during atrial-synchronized ventricular pacing, the ventricular event may be a premature ventricular contraction (PVC). A PVC occurs at a short ventricular interval from the most recent preceding ventricular event, paced or sensed, without an intervening atrial depolarization. The short ventricular interval ending on the PVC is typically followed by a long ventricular interval or ventricular pause. This short-long ventricular interval sequence can, under certain circumstances in some patients, lead to a ventricular tachyarrhythmia. As such, by controlling the ventricular pacing interval following a sensed ventricular event, e.g., an R-wave, the long post-sense ventricular interval may be avoided, reducing the likelihood of a subsequent tachyarrhythmia. In this way, the ventricular rate control techniques disclosed herein tend to increase the percentage of ventricular pacing pulses that are delivered synchronously with the atrial rate and promote a regular ventricular rate while minimizing the risk of ventricular tachyarrhythmia.

FIG. 1 is a conceptual diagram illustrating an implantable medical device (IMD) system 10 that may be used to sense cardiac signals and provide pacing therapy to a patient's heart 8. IMD system 10 includes a ventricular pacemaker 14. In some examples, pacemaker 14 is a leadless pacemaker, which may be configured as a transcatheter intracardiac pacemaker adapted for implantation wholly within a heart chamber, e.g., wholly within the RV or wholly within the left ventricle (LV) of heart 8. Pacemaker 14 may be reduced in size compared to subcutaneously implanted pacemakers and may be generally cylindrical in shape to enable transvenous implantation via a delivery catheter.

Pacemaker 14 is shown positioned along an endocardial wall of the RV, e.g., near the RV apex though other endocardial RV locations are possible, e.g., along the interventricular septum or the lateral free wall. Pacemaker 14 may be positioned within or on the right ventricle or left ventricle to provide respective right ventricular or left ventricular pacing according to the techniques disclosed herein. These techniques are not limited to a particular ventricular location and other positions than the position shown in FIG. 1 are possible. Furthermore, pacemaker 14 may be implanted in an atrial chamber for delivering ventricular pacing pulses from an atrial implant location. Pacemaker 14 may be positioned within the right atrium (RA), for example, for providing ventricular pacing from an atrial implant location, which may include ventricular pacing of myocardial tissue and/or the native ventricular conduction system, which includes the His bundle, the right and left bundle branches and the Purkinje fibers and may be referred to as the "His-Purkinje system. Another example of a pacemaker that may be configured to operate according to the techniques disclosed herein and is configured for delivering pacing to the ventricles from an atrial implant location is generally disclosed in U.S. Patent Application Publication No. 2019/0083800 A1 (Yang, et al., granted as U.S. Pat. No. 11,478, 653), incorporated herein by reference in its entirety.

Pacemaker 14 is capable of producing electrical stimulation pulses, e.g., pacing pulses, delivered to heart 8 via one or more electrodes on the outer housing of the pacemaker. Pacemaker 14 is configured to deliver RV pacing pulses and sense an RV cardiac electrical signal using housing based electrodes for producing an RV electrogram (EGM) signal. The cardiac electrical signals may be sensed using the housing based electrodes that are also used to deliver pacing pulses to the RV.

Pacemaker 14 is configured to control the delivery of ventricular pacing pulses to the ventricle in a manner that promotes synchrony between atrial activation and ventricular activation, e.g., by delivering ventricular pacing pulses at an atrioventricular (AV) interval after sensed atrial events. That is, pacemaker 14 controls pacing pulse delivery to maintain a desired AV interval between atrial contractions corresponding to atrial systole and ventricular pacing pulses delivered to cause ventricular depolarization and ventricular systole.

According to the illustrative examples described herein, atrial systolic events producing the active ventricular filling phase are detected by pacemaker 14 from a motion sensor such as an accelerometer enclosed by the housing of pacemaker 14. The motion signal produced by an accelerometer implanted within the RV includes motion signals caused by ventricular and atrial events. For example, acceleration of blood flowing into the RV through the tricuspid valve 16 between the RA and RV caused by atrial systole is detected by pacemaker 14 from the signal produced by an accelerometer included in pacemaker 14. Other motion signals detected by pacemaker 14, such as motion caused by ventricular contraction, motion caused by ventricular relaxation, and motion caused by passive filling of the ventricle are described below in conjunction with FIG. 4.

In other examples, pacemaker 14 may sense atrial systolic events by sensing atrial P-waves that are attendant to atrial depolarizations. P-waves are relatively low amplitude signals (e.g., compared to the R-waves) in the near-field RV electrical signal received by pacemaker 14. Atrial P-waves therefore can be difficult to consistently detect from the cardiac electrical signal acquired by pacemaker 14 implanted in or on a ventricular chamber. Therefore, in some examples, pacemaker 14 may include another sensor, such as a motion sensor, which may be an accelerometer, producing a signal for sensing cardiac mechanical events. Pacemaker 14 may be configured to sense an atrial event signal corresponding to atrial mechanical activation or atrial systole from the motion sensor signal. It is contemplated that other types of sensors of cardiac mechanical or hemodynamic function may be used to produce a cardiac mechanical signal to enable pacemaker 14 to sense atrial systolic event signals from the cardiac mechanical signal. Such sensors may include impedance sensors (which produce a signal correlated to blood volume in the ventricle), pressure sensors, acoustical sensors or other sensors that produce a signal correlated to the mechanical contractions of the heart chambers.

Ventricular pacing pulses are synchronized to the atrial event, which may be detected from the accelerometer signal as described below, by setting a programmable atrioventricular (AV) pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event and/or set sensing parameters used for discriminating the atrial systolic event from other cardiac motion events.

The AV pacing interval may be a programmed value selected by a clinician and is the time interval from the detection of the atrial event signal until delivery of the ventricular pacing pulse. In some instances, the AV pacing interval may be started from the time the atrial systolic event is sensed based on a motion sensor signal or starting from an identified fiducial point of the atrial event signal. The AV pacing interval may be identified as being hemodynamically optimal for a given patient based on clinical testing or assessments of the patient or based on clinical data from a population of patients. The AV pacing interval may be determined to be optimal based on relative timing of electrical and mechanical events as identified from the cardiac electrical signal received by pacemaker 14 and the motion sensor signal received by pacemaker 14. The AV pacing interval may be set to about 10 to 100 ms, in some examples, to control pacemaker 14 to deliver a ventricular pacing pulse synchronized to the atrial event sensed from the motion signal.

In some instances, the atrial event signal may not be sensed by pacemaker 14. For a variety of reasons such as atrial event signal undersensing or atrial fibrillation, a ventricular pacing pulse may not be followed by a sensed atrial event signal. In addition to setting the AV pacing interval, pacemaker 14 starts a ventricular pacing interval, which may be referred to as a VV pacing interval, in response to each delivered ventricular pacing pulse. The VV pacing interval may be set to a lower rate interval (LRI) which may correspond to a programmed lower rate, e.g., 40 to 60 beats per minute. If the VV interval expires without sensing an atrial event signal, pacemaker 14 delivers a ventricular pacing pulse at the VV pacing interval. As described herein the VV pacing interval set in response to a ventricular pacing pulse may be set to an RSI that is determined based on the actual ventricular rate, which may be faster than the programmed lower rate, to avoid abrupt changes in the ventricular rate when an atrial event is not sensed.

In other instances, an atrial event may not be sensed during a ventricular cycle when the pacemaker 14 senses a ventricular event, e.g., a ventricular R-wave from the cardiac electrical signal, before the atrial event. An early sensed ventricular event may be a PVC occurring at a relatively short ventricular interval. In order to avoid a subsequent long ventricular pause, pacemaker 14 may start a post-sense ventricular pacing interval in response to sensing a ventricular event before sensing an atrial event. The post-sense ventricular pacing interval may be set differently than the rate smoothing interval such that pacemaker 14 may set the VV pacing interval according to the rate smoothing interval when a ventricular pacing pulse is delivered and set the VV pacing interval according to the post-sense pacing interval when a ventricular event is sensed. Techniques for determining the rate smoothing interval and the post-sense pacing interval are described below. Both the rate smoothing interval and the post-sense pacing interval are determined for controlling the VV pacing interval in a manner that avoids abrupt changes in ventricular rate and short-long interval patterns that may be arrhythmogenic in some patients.

Pacemaker 14 may be capable of bidirectional wireless communication with another medical device implanted in the patient or external to the patient. For example, pacemaker 14 may be configured to communicate with external device 20 for programming the AV pacing interval, the LRI, and other pacing control parameters as well as both electrical and mechanical event sensing parameters utilized for detecting ventricular events and the atrial systolic events from the cardiac electrical signal and/or motion sensor signal. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 is configured for bidirectional communication with implantable telemetry circuitry included in pacemaker 14. External device 20 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link.

External device 20 may display data and information relating to pacemaker functions to a user for reviewing pacemaker operation and programmed parameters as well as EGM signals transmitted from pacemaker 14, motion sensor signals acquired by pacemaker 14, or other physiological data and pacing history data that is acquired by and retrieved from pacemaker 14 during an interrogation session.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in pacemaker 14, e.g., after viewing a visual representation of EGM, motion sensor signal and marker channel data.

Figure 2:
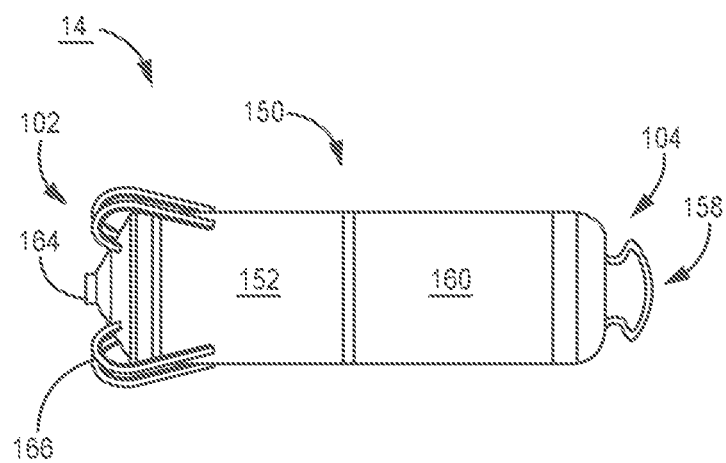
FIG. 2 is a conceptual diagram of the ventricular pacemaker shown in FIG. 1.

FIG. 2 is a conceptual diagram of pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along pacemaker 14 other than the locations shown.

In some examples, the distal tip electrode 164 may be configured as a tissue piercing electrode that can be inserted into cardiac tissue to advance electrode 164 to a desired pacing site. For example, distal tip electrode 164 may be a helical or other tissue piercing electrode that can be inserted into the inferior end of the interatrial septum, beneath the AV node and near the tricuspid valve annulus to position tip electrode 164 in, along or proximate to ventricular tissue, e.g., near the His bundle, for delivering ventricular pacing pulses.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Pacemaker 14 may include a set of fixation tines 166 to secure pacemaker 14 to cardiac tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
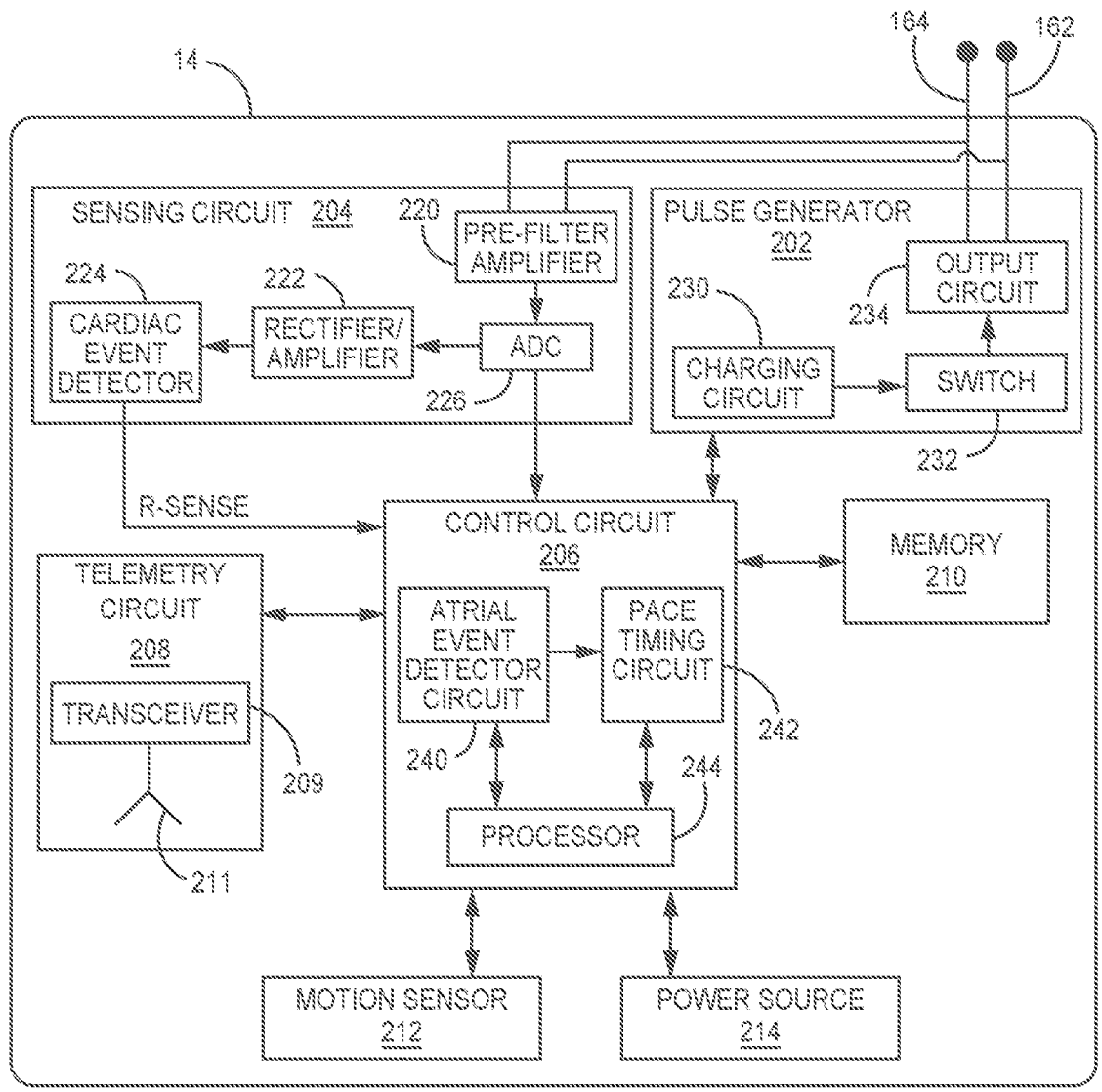
FIG. 3 is a schematic diagram of an example configuration of the pacemaker shown in FIG. 1.

FIG. 3 is a conceptual diagram of pacemaker 14 according to one example. Pacemaker 14 includes a pulse generator 202, a cardiac electrical signal sensing circuit 204, a control circuit 206, memory 210, telemetry circuit 208, motion sensor 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 is implemented as an accelerometer in the examples described herein and may also be referred to herein as "accelerometer 212." Motion sensor 212 is not limited to being an accelerometer, however, and other motion sensors or mechanical sensors may be utilized successfully in pacemaker 14 for detecting cardiac mechanical signals for use in sensing atrial events and controlling atrial synchronized ventricular pacing. Examples of motion sensors that may be implemented in motion sensor 212 include piezoelectric sensors and MEMS devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. The motion sensor 212 may include filters, amplifiers, rectifiers, an ADC and/or other components for producing a motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

Cardiac electrical signal sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to cardiac event detector 224.

Cardiac event detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the cardiac event detector 224 produces an R-wave sensed event signal (R-sense) that is passed to control circuit 206. In other examples, cardiac event detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

In some examples, cardiac event detector 224 is configured to sense P-waves from the cardiac electrical signal received by electrodes 162 and 164 (and/or other electrodes available on the pacemaker housing 150). Cardiac event detector 224 may compare the incoming signal to a P-wave sensing threshold and produce a P-wave sensed event signal passed to control circuit 206 in response to a threshold crossing. When pacemaker 14 is configured to sense R-waves and P-waves, sensing circuit 204 may include two different sensing channels, each including a pre-filter/amplifier, ADC, rectifier/amplifier and cardiac event detector configured to amplify and filter cardiac electrical signals received via one or two different sensing electrode pairs for separately sensing R-waves and P-waves from the cardiac electrical signals. The R-wave and P-wave sensing channels may share some components with separate R-wave and P-wave detectors each receiving a filtered, rectified signal in some examples. P-wave sensing may be used for verifying atrial events sensed from a motion sensor signal or vice versa. In some examples, P-wave sensed event signals are used by control circuit 206 for starting an AV pacing interval for controlling atrial synchronized ventricular pacing pulses delivered by pulse generator 202.

Control circuit 206 includes an atrial event detector circuit 240, pace timing circuit 242, and processor 244. Atrial event detector circuit 240 is configured to detect atrial mechanical events from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals, P-wave sensed event signals, and/or digital cardiac electrical signals from cardiac electrical signal sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14, depending on the pacing operating mode at the time the R-wave sensed event signal is received. As described below, control circuit 206 may start a VV pacing interval set to a post-sense ventricular pacing interval in response to an R-wave sensed event signal. R-wave sensed event signals may also be passed to atrial event detector circuit 240 for use in setting time windows used by control circuit 206 for detecting atrial systolic events from the motion sensor signal.

Atrial event detector circuit 240 receives a motion signal from motion sensor 212 and may start an atrial blanking period and/or an atrial refractory period in response to a ventricular electrical event, e.g., an R-wave sensed event signal from sensing circuit 204 or delivery of a ventricular pacing pulse by pulse generator 202. In some examples, atrial event detector circuit 240 determines if the motion sensor signal crosses an atrial event detection threshold outside the atrial refractory period. Atrial event detector circuit 240 may set time windows corresponding to the passive ventricular filling phase and the active ventricular filling phase based on the timing of a preceding ventricular electrical event, either an R-wave sensed event signal or a ventricular pacing pulse. A motion sensor signal crossing of an atrial event detection threshold during either of these windows may be detected as the atrial systolic event. As described below, two different atrial event detection thresholds may be established for applying during the respective passive filling phase window and active filling phase windows.

Atrial event detector circuit 240 passes an atrial event detection signal to processor 244 and/or pace timing circuit 242 in response to detecting an atrial systolic event from the motion sensor signal. In other examples, the atrial systolic event may be detected as a mechanical event from the motion sensor signal and/or as the electrical event (P-wave) by sensing circuit 204. A P-wave sensed event signal may be passed from cardiac event detector 224 to atrial event detector circuit 240 or directly to pace timing circuit 242. In still other examples, pacemaker 14 may be configured to receive a signal, e.g., via telemetry circuit 208, from another medical device indicating the timing of the atrial systolic event. Another medical device may be an intra-atrial pacemaker or a subcutaneously or submuscularly implanted sensing device, pacemaker or implantable cardioverter defibrillator configured to sense P-waves and transmit or broadcast a signal to pacemaker 14 to indicate the timing of a sensed P-wave or delivered atrial pacing pulse. Control circuit 206 may receive the transmitted signal, e.g., a radio frequency signal, a tissue conductance communication (TCC) signal or other transmitted signal via communication circuitry, e.g., telemetry circuit 208, as an atrial event signal for triggering a ventricular pacing pulse.

As indicated above, pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Pace timing circuit 242 may additionally include VV pacing interval timer for controlling the VV pacing interval set in response to a ventricular pacing pulse or in response to an R-wave sensed event signal. For example, if an atrial systolic event is not detected, e.g., from the motion sensor signal or based on P-wave sensing, for triggering a ventricular pacing pulse at the programmed AV pacing interval, a ventricular pacing pulse may be delivered by pulse generator 202 upon expiration of the VV pacing interval to prevent ventricular asystole and maintain a minimum ventricular rate. As described below, in order to avoid abrupt changes in ventricular rate and promote atrial event sensing recovery when an atrial event is not sensed during a cardiac cycle, control circuit 206 may be configured to set a VV pacing interval to an RSI during an atrial tracking ventricular pacing mode in response to a ventricular pacing pulse generated by pulse generator 202. The RSI may be determined based on one or more preceding paced ventricular event intervals. For example, the actual paced ventricular cycle lengths (VCLs) between consecutively delivered ventricular pacing pulses (Vp-Vp cycle lengths) and/or a sensed ventricular event and a subsequent pacing pulse (Vs-Vp cycle lengths) may be determined. An RSI may be set based on the actual paced VCLs so that a ventricular pacing pulse delivered in the absence of a sensed atrial event is delivered at a pacing interval that is within a predetermined interval of preceding paced VCLs, e.g., within 200 ms or within 100 ms or within 50 ms.

At times, control circuit 206 may control pulse generator 202 in a non-atrial tracking ventricular pacing mode (also referred to as "asynchronous ventricular pacing") during which a VV pacing interval may be set based on a patient activity metric determined from motion sensor 212 or according to a programmed lower rate. If control circuit 206 switches from an atrial-tracking ventricular pacing mode to a non-atrial tracking ventricular pacing mode, control circuit 206 may set RSIs to control a gradual adjustment of the ventricular pacing rate from the atrial tracking paced VCLs to a ventricular lower rate used to control the ventricular pacing rate during the asynchronous ventricular pacing mode, e.g., a VVI or VDI pacing mode.

Processor 244 may retrieve other programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, processor 244 may provide sensing control signals to sensing circuit 204, e.g., R-wave sensing threshold, P-wave sensing threshold, sensitivity, and/or various blanking and refractory intervals applied to the cardiac electrical signal.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval or a VV pacing interval and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Memory 210 may store one or more paced VCLs for use by control circuit 206 in determining an RSI. In some examples, the most recent paced VCL (ending with a ventricular pacing pulse) is determined as an actual ventricular pacing rate for use in setting the RSI. In other examples, memory 210 may buffer a series of paced VCLs for determining an actual ventricular pacing rate as the mean, median, nth longest, or other metric of the paced VCLs. The VCL metric may be used by processor 244 for determining a rate smoothing pacing interval. For instance, pace timing circuit 242 may include a timer or counter that is started upon delivery of a ventricular pacing pulse or receiving a ventricular sensed event signal and is used to determine the paced VCL until the next delivered ventricular pacing pulse. The paced VCL may be stored in memory 210, e.g., in a first-in-first-out buffer of a predetermined number of paced VCLs. In one example, up to 12 paced VCLs are stored for determining a median paced VCL, though more than or less than 12 paced VCLs, e.g., 8 paced VCLs, may be stored for determining a mean or median paced VCL.

Processor 244 may be configured to set the RSI to a predetermined increment greater than the actual ventricular pacing rate, which may be determined based on a single most recent paced VCL or a median or mean of multiple paced VCLs in some examples. In some examples, processor 244 determines a rate smoothing base interval (RSBI) based on the most recent paced VCL. The RSBI may be initialized to the programmed LRI. The RSBI may be compared to the next paced VCL. If the RSBI is greater than the next paced VCL, it is decreased by an adjustment interval, e.g., by 8 to 20 ms. If the RSBI is less than the next paced VCL, it is increased by the adjustment interval. If the RSBI is equal to (or within an adjustment interval) of the most recent paced VCL, it is not adjusted and remains at its current value. In this way, control circuit 206 may update the RSBI on each paced VCL to track the actual paced ventricular rate on a beat by beat basis. The RSI may be updated each time the RSBI is updated by adding the predetermined increment to the RSBI. In other examples, the RSI in updated every M ventricular cycles, e.g., every eight ventricular cycles by adding the predetermined increment to the current value of the RSBI.

The predetermined increment may be set to 10 ms, 25 ms, 50 ms, 75 ms, 100 ms, 150 ms, 200 ms, 250 ms or other selected time interval. In some examples, the increment may be set by control circuit 206 according to the current RSBI, mean or median paced VCL or other metric of heart rate. A lower increment may be used during relatively higher heart rates and a higher increment may be used during relatively lower heart rates. The increment may be set as a percentage of the heart rate metric, such as 8%, 10%, 12%, 15%, or 20% as examples. In other examples, different fixed increments may be set for different heart rate ranges. For example when the heart rate metric (RSBI, median paced VCL, or the like) is less than or equal to 80 beats per minute, the predetermined increment may be set to 100 ms. When the heart rate metric is greater than 80 beats per minute, the increment may be set to 50 ms. It is to be understood that more than two fixed predetermined increments may be stored in memory 210, e.g., in a look-up table, in conjunction with a corresponding heart rate range, to be used by control circuit 206 for setting the RSI.

Processor 244 may control pace timing circuit 242 to start a VV pacing interval timer or counter to time out the RSI in response to delivery of a ventricular pacing pulse. If the RSI expires without an atrial systolic event being sensed, a ventricular pacing pulse is delivered at the expiration of the RSI by pulse generator 202.

Memory 210 may additionally or alternatively store one or more VCLs for use by control circuit 206 in determining a post-sense pacing interval. A Vx-Vs cycle length is a VCL ending with a ventricular sensed event signal (Vs) received from cardiac event detector 224 and beginning with the most recent preceding ventricular event, Vx, which may be either a ventricular pacing pulse or a preceding ventricular sensed event, e.g., a sensed R-wave. Thus, a stored Vx-Vs cycle length may be a Vs-Vs cycle length or a Vp-Vs cycle length. One or a series of sensed VCLs (ending with a ventricular sensed event signal) may be stored in memory 210 in a first-in-first-out basis for use by control circuit 206 in determining the post-sense pacing interval.

Processor 244 may be configured to set the post-sense pacing interval to a predetermined increment greater than the most recent sensed VCL, ending with the current ventricular sensed event. In other examples, processor 244 may set the post-sense pacing interval to a predetermined increment greater than a median or mean of multiple sensed VCLs in some examples. The predetermined increment used to set the post-sense pacing interval may be the same or different than the increment used to set the RSI. The predetermined increment may be 100 to 300 ms, or about 200 ms as examples. The predetermined increment may be a fixed increment set based on a heart rate metric, e.g., the current sensed VCL or a mean or median sensed VCL. In other examples, the increment may be set as a percentage of the current sensed VCL or mean or median sensed VCL. As described below, the post-sense pacing interval may be set as a sensed VCL plus an increment but not less than a minimum post-sense pacing interval, e.g., not less than 700 ms, 750 ms or 800 ms, and not greater than a maximum post-sense pacing interval, e.g., 1000 ms or the programmed lower rate interval.

Processor 244 may control pace timing circuit 242 to start a VV pacing interval timer or counter to time out the post-sense pacing interval set in response to receiving a ventricular sensed event signal from cardiac electrical signal sensing circuit 204. If the post-sense pacing interval expires without an atrial event being sensed or another ventricular event being sensed, a ventricular pacing pulse is delivered at the expiration of the post-sense pacing interval by pulse generator 202. When an atrial event is sensed, the post-sense pacing interval is cancelled or suspended without expiring. The AV pacing interval is started in response to the sensed atrial event, and the VV pacing interval is set to the RSI upon delivery of the ventricular pacing pulse at the expiration of the AV pacing interval. As described below, e.g., in conjunction with FIGS. 8 and 9, in some examples, the VV pacing interval may be set to a temporary post-pace pacing interval instead of the RSI when control circuit 206 determines that rate smoothing criteria are not met.

Power source 214, which may correspond to battery subassembly 160 in FIG. 2, provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed, power to transceiver 209, motion sensor 212, and ADC 226 and other circuitry of sensing circuit 204 as needed as well as memory 210.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Figure 4:
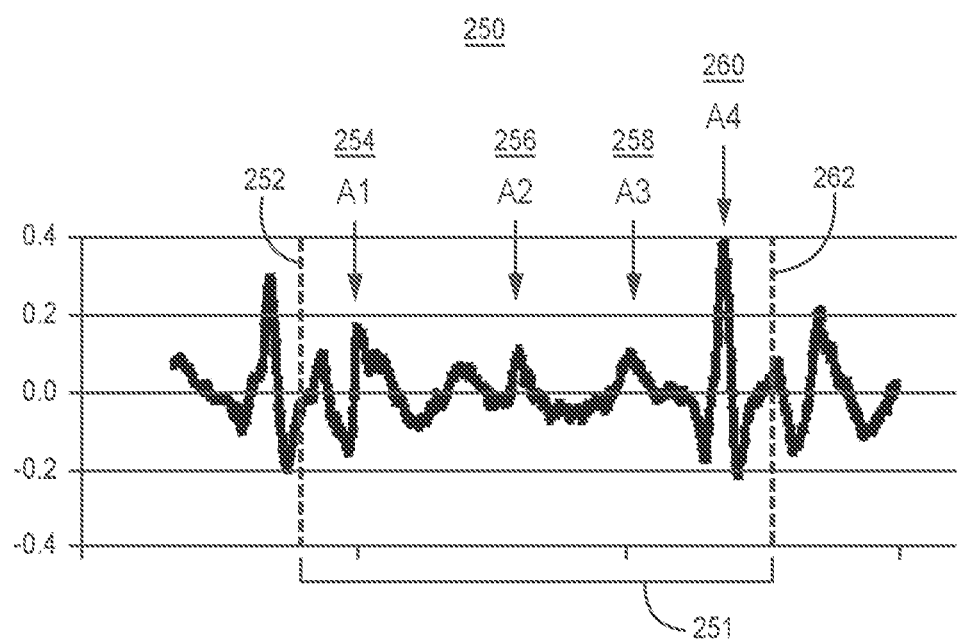
FIG. 4 is an example of a motion sensor signal that may be acquired by the pacemaker of FIG. 1 over a ventricular cycle.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251, which may be referred to as one cardiac cycle including one ventricular systolic phase and one ventricular diastolic phase. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A2 event 265 is an acceleration signal that occurs during ventricular relaxation and marks the approximate offset or end of ventricular mechanical systole. The A2 event 256 may occur with closure of the aortic and pulmonic valves, marking the approximate offset or end of ventricular mechanical systole.

The A3 event 258 is an acceleration signal that occurs during passive ventricular filling and marks ventricular mechanical diastole. Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 may also be referred to herein as the "atrial systolic event" or merely the "atrial event." The A4 event 260 is the atrial event that is detected or sensed from motion sensor signal 250 by atrial event detector circuit 240. Pace timing circuit 242 may trigger delivery of a ventricular pacing pulse by starting the AV pacing interval in response A4 event 260 being detected. Control circuit 206 may optionally be configured to detect one or more of the A1, A2, and A3 events from motion sensor signal 250, for at least some ventricular cardiac cycles, for use in positively detecting the A4 event 260 and/or for use in setting atrial event detection control parameters. The A1, A2 and/or A3 events may be detected and characterized to avoid false detection of A4 events and promote reliable A4 event sensing for proper timing of atrial-synchronized ventricular pacing pulses.

Figure 5:
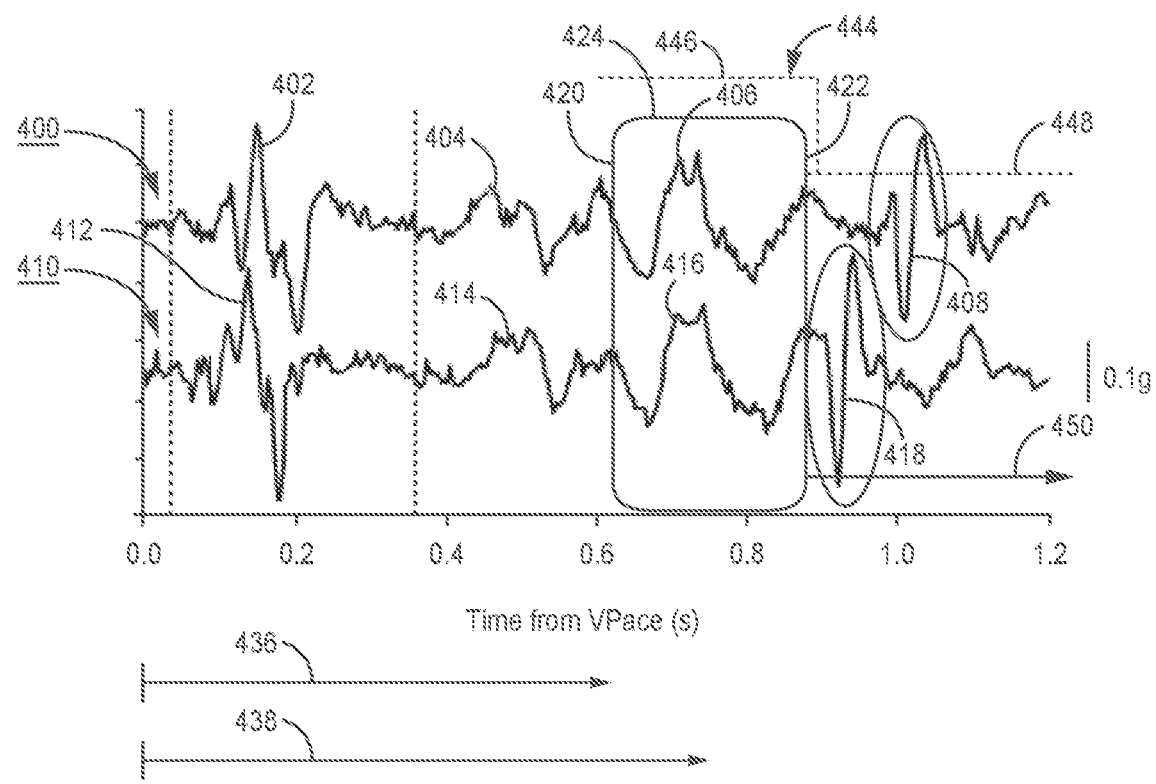
FIG. 5 is an example of motion sensor signals acquired over two different cardiac cycles.

FIG. 5 is an example of motion sensor signals 400 and 410 acquired over two different cardiac cycles. A ventricular pacing pulse is delivered at time 0.0 seconds for both cardiac cycles. The top motion sensor signal 400 is received over one cardiac cycle, and the bottom motion sensor signal 410 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that control circuit 206 may receive a digitized filtered, amplified and rectified signal from motion sensor 212 for processing and analysis as described in conjunction with the accompanying drawings.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (which may mark the end of ventricular systole and the isovolumic ventricular relaxation phase) and the A3 events 406 and 416 (occurring during passive ventricular filling) are well-aligned in time. Since the A1, A2 and A3 events are ventricular events, occurring during ventricular contraction, at the end of ventricular systole and during passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of ventricular A1, A2 and A3 events to each other and the immediately preceding ventricular electrical event is expected to be consistent from beat-to-beat.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which may extend from the ventricular electrical event (at time 0.0) through an estimated onset of ventricular diastole so that the atrial blanking period 436 includes both the A1 and A2 events in some examples. An A3 window 424 may be set having a starting time 420 corresponding to the end of the post-ventricular atrial blanking period 436 and having an ending time 422. The ending time 422 may be adjusted using techniques described herein, e.g., below in conjunction with FIGS. 12-14. The ending time 422 may also be considered a starting time of an A4 sensing window 450, though A4 events may be sensed during the A3 window in some instances. The A3 window 424 is also referred to here as a "ventricular diastolic event window," and ending time 422 is also referred to herein as a "ventricular diastolic event window ending time" since the A3 event corresponding to passive ventricular filling, a ventricular diastolic event, is expected to occur during the A3 window, before ending time 422.

A4 events 408 and 418 may be detected based on a multi-level A4 sensing threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 sensing threshold amplitude 446 may be established for detecting an early A4 event that is fused with the A3 event during the A3 window 424. A second, lower A4 sensing threshold amplitude 448 may be established for detecting relatively later A4 events, after the ending time 422 of the A3 window 424, during an A4 window 450. The A4 window 450 extends from the ending time 422 of the A3 window 424 until the next ventricular electrical event, sensed or paced. The earliest crossing of the A4 sensing threshold 444 by the motion sensor signal after the starting time 420 of the A3 window (or after the expiration of the atrial blanking period 436) may be detected as the atrial systolic event. Atrial event detector circuit 240 may sense the A4 event in response to the earliest crossing time of the high A4 sensing threshold amplitude or the low A4 sensing threshold amplitude.

In some examples, control circuit 206 may set a post-ventricular atrial refractory period (PVARP) 438. The PVARP 438 may extend from the ventricular electrical event (sensed R-wave or ventricular pacing pulse) for a time interval longer than the post-ventricular atrial blanking period 436. Depending on the end time 422 of the A3 window 424, the PVARP 438 will generally expire during the A3 window 424. When the motion sensor signal crosses the high A4 sensing threshold amplitude 446 during the PVARP 438, but outside the blanking period 436, a refractory A4 sense may be made by atrial event detector circuit 240. Pace timing circuit 242 does not set an AV pacing interval in response to a refractory A4 sense, but control circuit 206 may use the refractory A4 sense in adjusting A4 sensing control parameters. When the motion sensor signal crosses the A4 sensing threshold 444 after the expiration of PVARP 438, atrial event detector circuit 240 senses the atrial systolic event, and pacing timing circuit 242 starts an AV pacing interval (not shown in FIG. 5). Upon expiration of the AV pacing interval, pulse generator 202 generates a pacing pulse delivered to the ventricle to track the non-refractory sensed atrial event.

Various examples of a ventricular pacemaker configured to detect atrial systolic events from a motion sensor signal for delivering atrial synchronized ventricular pacing are disclosed in commonly-assigned U.S. Pat. No. 10,532,212 (Splett et al.), U.S. Pat. No. 10,449,366 (Splett, et al.), U.S. Pat. No. 10,286,214 (Demmer, et al.), U.S. Pat. No. 10,328,270 (Demmer, et al.) and U.S. Pat. No. 10,207,116 (Sheldon, et al.), all of which are incorporated herein by reference in their entirety. The techniques disclosed herein for controlling the timing of ventricular pacing pulses using rate smoothing pacing intervals, temporary post-pace ventricular pacing intervals, and post-sense ventricular pacing intervals may be implemented in conjunction with any of the examples of atrial event sensing presented in the foregoing incorporated references. Furthermore, the techniques for controlling the VV pacing interval as described herein may be implemented in a variety of pacemakers capable of sensing atrial events and delivering atrial synchronous ventricular pacing. The techniques for controlling the VV pacing intervals as described herein are not limited for use with any particular method or type of sensor used for sensing the atrial events (e.g., atrial P-waves or atrial contractions) that trigger synchronous ventricular pacing pulses.

Figure 6:
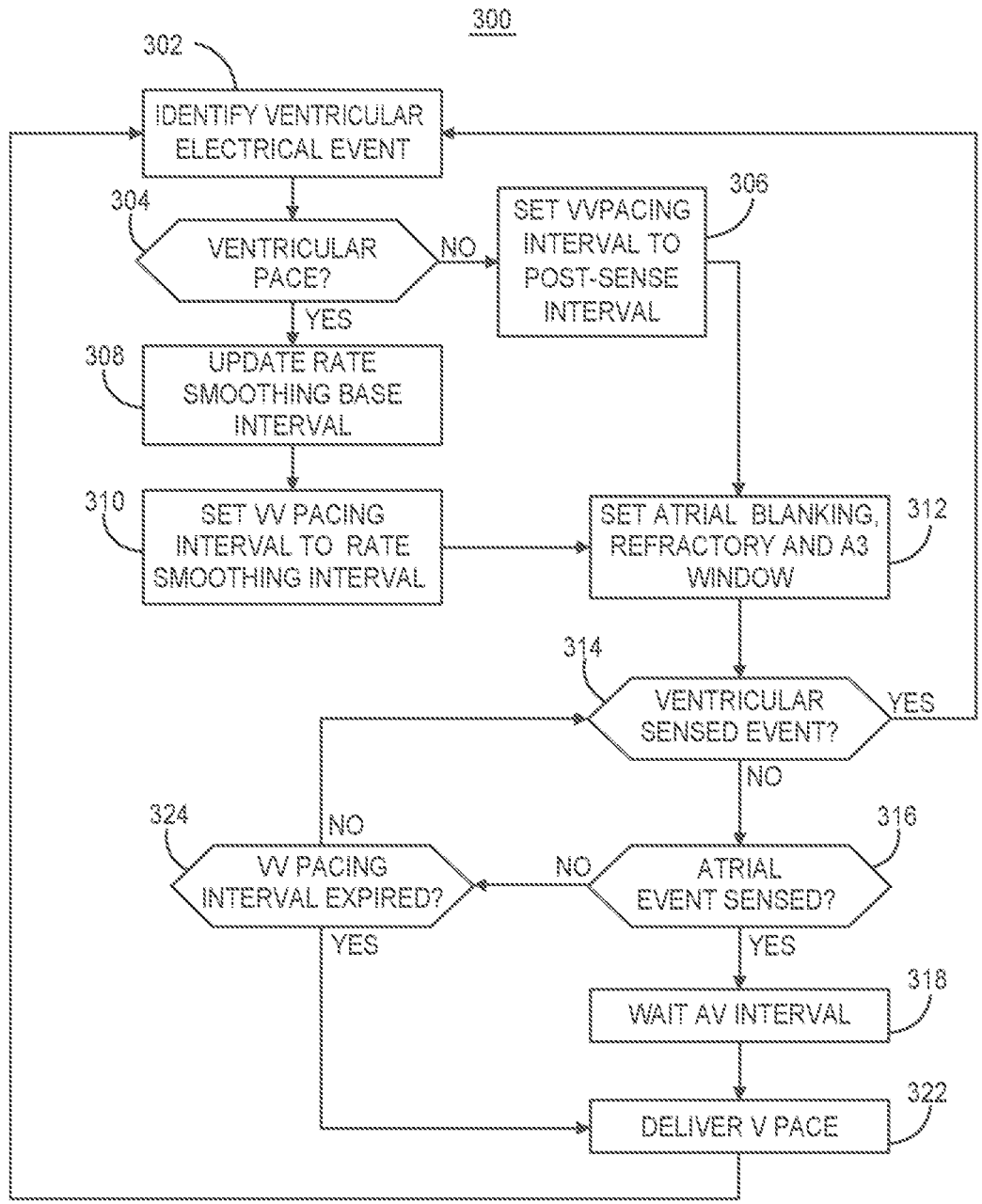
FIG. 6 is a flow chart of a method for controlling ventricular pacing pulses delivered by a pacemaker according to some examples.

FIG. 6 is a flow chart 300 of a method for controlling ventricular pacing pulses delivered by a pacemaker, such as pacemaker 14, according to some examples. At block 302, control circuit 206 of pacemaker 14 identifies a ventricular electrical event. The ventricular event may be a ventricular pacing pulse delivered by pulse generator 202 or a ventricular sensed event corresponding to an intrinsic R-wave attendant to the depolarization of the ventricular myocardium. Control circuit 206 may identify the ventricular electrical event as a sensed event, e.g., corresponding to a sensed intrinsic R-wave, upon receiving a ventricular sensed event signal from sensing circuit 204. When the ventricular electrical event identified at block 302 is a sensed event and not a ventricular paced event (as determined at block 304), control circuit 206 determines and starts a post-sense ventricular pacing interval at block 306.

Generally, atrial synchronous ventricular pacing is being delivered in a patient having AV block. Atrial depolarizations are either not conducted to the ventricles or may be conducted at a very long delay such that ventricular pacing is needed. Some patients having some degree of AV block, however, may experience episodes of AV conduction and/or premature ventricular contractions (PVCs). When AV conduction or a PVC does occur, resulting in a sensed ventricular event, control circuit 206 may set the VV pacing interval to the post-sense ventricular pacing interval at block 306. The post-sense ventricular pacing interval is determined by control circuit 206 based on at least one most recent VCL in some examples. Techniques for determining the post-sense ventricular pacing interval are described below in conjunction with FIG. 7. The post-sense ventricular pacing interval is set to promote sensing of the A4 event during the next ventricular cycle following the ventricular sensed event, while avoiding a long ventricular interval that may occur, particularly following a PVC, setting up a short-long pattern of ventricular cycles.

If the ventricular electrical event identified at block 302 is a ventricular pacing pulse (as determined at block 304), control circuit 206 may update rate smoothing base interval (RSBI) at block 308. The RSBI may be based on the actual paced ventricular rate. In some examples, the RSBI is set based on the most recent paced VCL ending with the ventricular pacing pulse identified at block 302. The paced VCL may or may not include an intervening sensed atrial event. The paced VCL may have a starting ventricular event that is a ventricular pacing pulse or a ventricular sensed event in some instances. The ending ventricular pacing pulse may be delivered at an AV interval from a sensed atrial event (or signal corresponding thereto), in which case the actual paced ventricular rate is the rate from the most recent preceding ventricular event to the atrial synchronous pacing pulse. The ending ventricular pacing pulse may be delivered at a VV pacing interval following a preceding paced or sensed ventricular event when the atrial event is not sensed.

Control circuit 206 may set the RSBI based on the paced VCL by comparing the current value of the RSBI to the paced VCL. In some examples, the RSBI is set equal to the VCL. In other examples, the RSBI is adjusted to track toward the VCL beat by beat. For example, control circuit 206 may compare the current value of the RSBI to the current paced VCL. When the RSBI is greater than the current paced VCL, the RSBI is decreased by an adjustment interval toward the VCL. When the RSBI is less than the current VCL, the RSBI is increased by the adjustment interval toward the VCL. When the RSBI is equal to or within the adjustment interval of the VCL, the RSBI is held constant. The adjustment interval may be between 8 and 20 ms, as examples. The adjustment interval may be fixed or scaled based on the VCL, based on the current value of the RSBI, and/or based on the difference between the VCL and the RSBI. For instance, the adjustment interval may be set to a percentage of the VCL, a percentage of the RSBI or a percentage of the difference between the VCL and the RSBI. In other examples, the adjustment interval may be predefined to be a first interval for a first range of the difference between the VCL and the RSBI and defined to be second interval for second range of the difference between the VCL and the RSBI. To illustrate, when the difference between the VCL and the RSBI is 100 ms or more, the adjustment interval may be set to 20 ms. When the difference between the VCL and the RSBI is less than 100 ms, the adjustment interval may be set to 10 ms. In this way, rapid changes or fluctuations in the RSBI are avoided when the RSBI and the VCL are close in value. When the RSBI and the VCL are further apart, a larger adjustment interval allows the RSBI, and subsequently the RSI, to be adjusted more quickly, e.g., within a fewer number of ventricular cycles, to the current paced VCL. In this way, as the actual ventricular paced rate increases or decreases with changes in the atrial rate during atrial synchronous ventricular pacing, the RSBI tracks the actual ventricular paced rate.

In another example, a median paced VCL may be determined by control circuit 206 at block 308 for use in updating the RSBI. The median paced VCL may be determined from the most recent six to twelve paced VCLs, or another selected number of VCLs. Each paced VCL is the time interval between two consecutive ventricular pacing pulses (or corresponding pacing evoked R-waves) and/or between a sensed ventricular event and subsequent ventricular pacing pulse. In other examples, only paced VCLs beginning and ending with a ventricular pacing pulse are used to update the RSBI. For instance, the paced VCLs may be determined as paced intervals between two consecutive ventricular pacing pulses without any intervening ventricular sensed event signals in some examples. Since the patient may have complete AV block, any intrinsically sensed R-wave may be a PVC. The short interval preceding the PVC, which may start with a ventricular pacing pulse, and a long interval that may follow a PVC and end with a ventricular pacing pulse, may be ignored in determining an updated RSBI at block 308 because these intervals associated with a PVC are not representative of the regular, ventricular paced rate. The RSBI may be set equal to an updated mean or median paced VCL at block 308. In other examples, the RSBI may be updated by adding or subtracting an adjustment interval to the current RSBI value based on a comparison of the current RSBI to the mean or median VCL (or another metric of the paced VCLs), as generally described above in the examples of setting the RSBI plus or minus an adjustment interval based on a comparison to the most recent paced VCL.

Control circuit 206 determines the RSI at block 310 by adding a rate smoothing increment to the RSBI and starts the RSI in response to the delivered ventricular pacing pulse (identified at block 304). The RSI is the VV pacing interval that is set in response to the ventricular pacing pulse to control the timing of the next ventricular pacing pulse in the absence of a sensed atrial event (or a sensed ventricular event). Instead of scheduling a ventricular pacing pulse at a programmed LRI following each ventricular pacing pulse, when an atrial event is not sensed, the VV pacing interval set to the RSI promotes ventricular pacing at or near an expected atrial rate based on the preceding actual, atrial synchronous ventricular pacing rate. The RSI avoids an abrupt ventricular rate change and preserves the timing of the post-ventricular atrial blanking period and the start and end of the A3 window relative to a preceding ventricular pacing pulse and the next anticipated atrial event to promote a rapid return to atrial sensing if the VV pacing interval expires without an atrial sensed event. In various examples, the RSI is started at block 310 only in response to a delivered ventricular pacing pulse, which may be delivered upon expiration of a preceding AV pacing interval or a VV pacing interval.

Along with starting the VV pacing interval set to either the post-sense pacing interval at block 306 or the RSI at block 310, control circuit 206 may start an atrial blanking period and a PVARP at block 312 (e.g., as shown in FIG. 5). Additionally control circuit 206 may set the A3 window ending time in response to each identified ventricular event, sensed or paced. An atrial event sensed during the PVARP may not be used to start an AV pacing interval. Upon expiration of the atrial blanking period, control circuit 206 may start the A3 (passive ventricular filling) window that is terminated according to the A3 window end time, e.g., as shown in FIG. 5.

If a ventricular event is sensed before the VV pacing interval expires, as determined at block 314, control circuit 206 returns to block 302. The scheduled pacing pulse is withheld, and control circuit 206 may determine the sensed VCL for setting the post-sense ventricular pacing interval at block 306.

As long as a ventricular event is not sensed at block 314, control circuit 206 waits for an atrial event to be sensed at block 316. If an atrial event is not sensed ("no" branch of block 316), the VV pacing interval continues to run (block 324). If an atrial event is sensed at block 316, control circuit 206 responds by starting the AV pacing interval at block 318. The atrial event may be sensed from the motion sensor signal in response to an A4 sensing threshold crossing. As described above, a higher A4 sensing threshold may be applied during the A3 window and a lower A4 sensing threshold may be applied starting from the end of the A3 window until either an A4 event is sensed or a ventricular pacing pulse is delivered (or intrinsic R-wave is sensed). In other examples, the atrial event may be a P-wave sensed from a cardiac electrical signal. In still other examples, the atrial event sensed at block 316 may be a communication signal or trigger signal transmitted by another co-implanted medical device and received by pacemaker 14 to indicate that an atrial P-wave or atrial pacing pulse has occurred.

At block 322, control circuit 206 delivers a ventricular pacing pulse upon expiration of the AV interval. The VV pacing interval that may still be running at the time of the sensed atrial event is canceled, and a ventricular pacing pulse scheduled at the expiration of the VV pacing interval is withheld. Control circuit 206 returns to block 302 and updates the RSBI at block 308 using the most recent paced VCL. It is to be understood that in some examples, an R-wave may be sensed during the AV interval at block 318, in which case the AV interval may be suspended and the corresponding scheduled ventricular pacing pulse may be withheld. In this case, the process returns to block 302 without delivering an atrial synchronized ventricular pacing pulse.

If an atrial event is not sensed ("no" branch of block 316) and the VV pacing interval expires at block 324, a ventricular pacing pulse is delivered at the expiration of the VV pacing interval at block 322. When a ventricular pacing pulse is delivered at the RSI from a preceding ventricular pacing pulse, the RSI will be used to update the RSBI at block 308. The RSBI may be updated based on the single, preceding paced VCL or determined based on multiple preceding paced VCLs, e.g., based on a mean or median value as described above. If multiple ventricular pacing pulses are delivered at RSIs on consecutive cycles without atrial sensed events or at increasing VCLs that include atrial sensed events (with ventricular pacing pulses delivered at the AV interval), the RSIs will gradually increase toward the programmed LRI since each RSI is based on the updated RSBI plus a rate smoothing increment, e.g., 8 to 200 ms. If atrial sensing is lost for multiple cardiac cycles, the RSI gradually increases and approaches the LRI. If the LRI is reached, the RSI set in response to a ventricular pacing pulse is not set to be greater than the LRI. In other words, the maximum possible RSI (and the maximum possible post-sense ventricular pacing interval) may be equal to the LRI.

When the VV pacing interval that expires at block 324 is set to the post-sense pacing interval, the ventricular pacing pulse delivered at block 322 occurs at a paced VCL equal to the post-sense pacing interval. The post-sense pacing interval may be used to update the RSBI at block 308 in some examples such that the VV pacing interval set to the RSI at block 310 takes into account the paced VCL ending on the post-sense pacing interval. In other examples, the RSBI may not be adjusted at block 308 based on the paced VCL equal to the post-sense pacing interval such that the RSI may remain at its current value, without adjustment. The VV pacing interval may be set to the previously determined RSI at block 310, without adjustment, in response to a ventricular pacing pulse delivered at the post-sense pacing interval.

Figure 7:
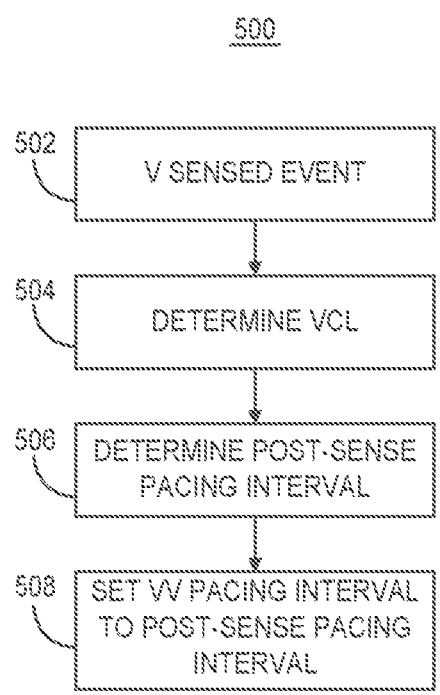
FIG. 7 is a flow chart of a method for determining a post-sense pacing interval according to one example.

FIG. 7 is a flow chart 500 of a method for setting the post-sense pacing interval according to one example. The process of flow chart 500 may be performed at block 306 of FIG. 6 in some examples. When control circuit 206 identifies a ventricular sensed event (block 502), e.g., by receiving an R-wave sensed event signal from sensing circuit 204, control circuit 206 determines the sensed VCL ending with the sensed ventricular event at block 504 and starting with the most recent preceding ventricular event. The most recent preceding ventricular event may be a ventricular pacing pulse or a sensed ventricular event.

Control circuit 206 determines the post-sense pacing interval at block 506 based on at least the VCL determined at block 504. In some examples, the post-sense pacing interval is determined based on only the most recent sensed VCL. Control circuit 206 may add a predetermined increment to the sensed VCL. The predetermined increment may be between 100 and 300 ms, or between 150 and 250 ms, and is 200 ms in one example. Alternatively, control circuit 206 may determine the post-sense pacing interval as a predetermined percentage of the sensed VCL, e.g., 110%, 120%, or 130% of the sensed VCL.

Determination of the post-sense pacing interval by control circuit 206 at block 506 may include limiting the maximum and minimum values of the post-sense pacing interval determined based on the most recent sensed VCL. For instance, the post-sense pacing interval may be set to the greater one of a fixed minimum post-sense pacing interval and the most recent sensed VCL plus the predetermined increment. The fixed minimum post-sense pacing interval may be set to between 700 and 900 ms or about 800 ms in some examples.

When the most recent sensed VCL plus the predetermined increment is greater than the minimum post-sense pacing interval, control circuit 206 sets the post-sense pacing interval to the smallest one of a post-sense pacing interval maximum limit and the most recent sensed VCL plus the predetermined increment. The maximum limit may be set to the programmed LRI. For example, if the ventricular lower rate is programmed to 40 beats per minute, the post-sense pacing interval maximum limit is 1500 ms. In an illustrative example, control circuit 206 determines the post-sense pacing interval at block 506 to be the greater one of a fixed minimum interval of 800 ms or the sensed VCL plus the predetermined increment but not greater than the maximum limit of 1500 ms, the programmed LRI. In other examples, the maximum limit may be set differently than the LRI, e.g., less than the LRI. For instance, when the programmed lower rate is 40 beats per minute, the post-sense pacing interval maximum limit may be programmable to 1000 ms, 1200 ms or other value up to the LRI. The post-sense pacing interval minimum limit may be programmable to 600 ms, 700 ms, 800 ms or 900 ms, as examples. Control circuit 206 may determine the post-sense pacing interval at block 506 to be the most recent sensed VCL plus 200 ms (or another predetermined increment) within the established minimum and maximum limits, for example. In this way, the post-sense pacing interval provides rate smoothing following a ventricular sensed event, and by setting minimum and maximum limits a very short pacing interval is avoided when a PVC occurs at a short interval and a very long pacing interval is avoided when a long pause follows a PVC. The minimum and maximum limits have the effect of adding a relatively longer increment when the sensed VCL is very short and a relatively shorter increment when the sensed VCL is very long.

In other examples, when more than one sensed VCL occurs consecutively or within a predetermined number of recent ventricular events, control circuit 206 may determine a mean or median sensed VCL or other metric of multiple sensed VCLs. For example, a run of PVCs may occur resulting in a series of two or more sensed VCLs. Control circuit 206 may determine a metric of two or more sensed VCLs that occur consecutively or within a short time interval of each other, e.g., within the last two to eight VCLs and set the post-sense pacing interval based on the metric of multiple sensed VCLs in some instances.

At block 508, control circuit 206 starts the VV pacing interval set to the determined post-sense pacing interval. If the VV pacing interval expires without another ventricular sensed event or an atrial sensed event, pulse generator 202 generates a ventricular pacing pulse in response to the expiration of the VV pacing interval. In this way, when the ventricular sensed event is a PVC, the next ventricular cycle is limited in length to the post-sense pacing interval, instead of a long pause that can follow a PVC, thereby avoiding a short-long ventricular cycle pattern.

Figure 8:
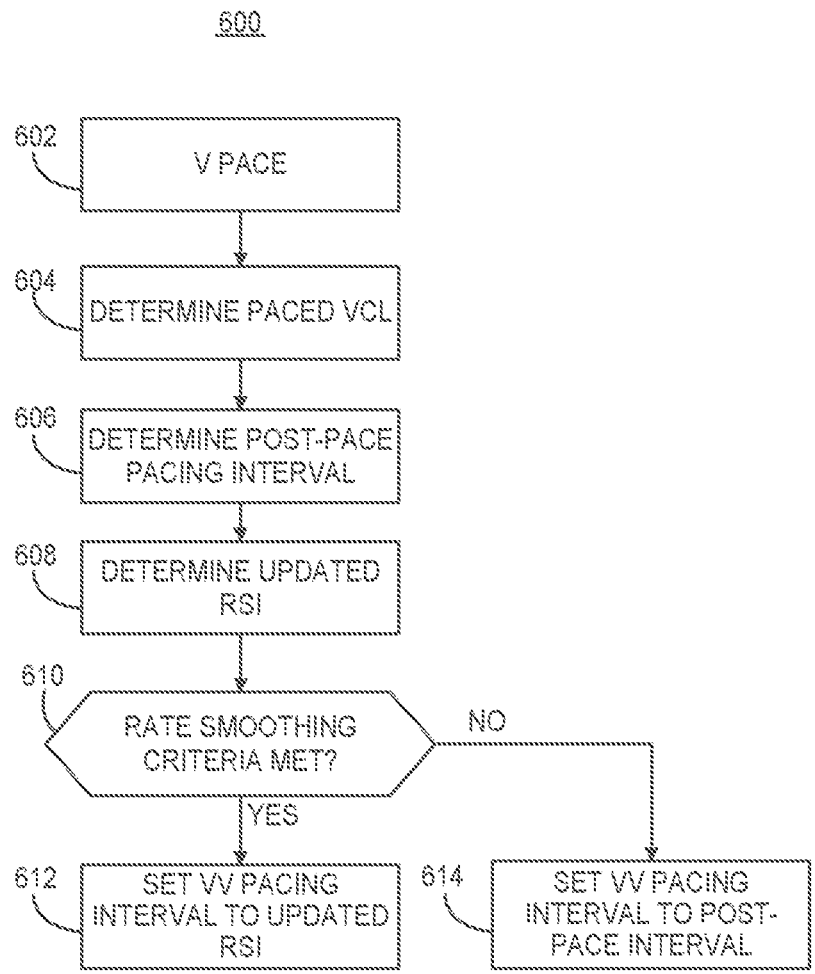
FIG. 8 is a flow chart of a method for setting a VV pacing interval in response to a ventricular pacing pulse according to some examples.

FIG. 8 is a flow chart 600 of a method for setting the VV pacing interval in response to a ventricular pacing pulse according to some examples. As described above in conjunction with FIG. 6, control circuit 206 may set the VV pacing interval to the RSI in response to a ventricular pacing pulse and to the post-sense pacing interval in response to a ventricular sensed event. In some instances, the RSI set based on a RSBI may have not reached an appropriate value to provide rate smoothing. If the pacing mode has recently changed or if atrial events are not being sensed regularly, the paced VCLs may be too few or irregular for the RSBI to reach a value that is closely tracking the paced VCLs. As such, control circuit 206 may be configured to set the VV pacing interval to either a temporary post-pace pacing interval or the RSI in response to a ventricular pacing pulse, depending on whether rate smoothing criteria are met, as described below.

At block 602, pulse generator 202 generates a ventricular pacing pulse in response to the expiration of a pacing interval. The pacing interval may be an AV pacing interval set in response to a sensed atrial event. The pacing interval may be a VV pacing interval set in response to a ventricular pacing pulse or a sensed ventricular event.

In response to the generated ventricular pacing pulse, control circuit 206 determines the paced VCL at block 604. The paced VCL may start with a most recent preceding ventricular pacing pulse or a ventricular sensed event. At block 606, control circuit 206 determines a post-pace pacing interval based on the paced VCL. The post-pace pacing interval may be determined as the paced VCL plus a predetermined increment, e.g., 50 to 200 ms, or the paced VCL plus a predetermined percentage of the paced VCL, e.g., 5%, 10%, 15%, 20% or other selected percentage.

At block 608, control circuit 206 may determine an updated RSI. The RSI may be determined based on one or more recent paced VCLs as described in any of the examples herein. For example, the RSI may be determined from a RSBI that is updated based on the most recent paced VCL as described above. Example methods that may be used for determining an RSI are generally disclosed in U.S. Patent Publication No. 2019/0321634 A1 (Sheldon, et al.), incorporated herein by reference in its entirety.

At block 610, control circuit 206 determines if rate smoothing criteria are met. Example techniques for determining when rate smoothing criteria are met are described below in conjunction with FIG. 9. In various examples, rate smoothing criteria may be met when the ventricular rate is stable, ventricular pacing is tracking sensed atrial events, a pacing mode switch or programmable control parameter change has not occurred recently (e.g., within the last 5 to 20 ventricular pacing pulses), and/or the current RSI is at least equal to the median VCL. Additionally or alternatively, the rate smoothing criteria are satisfied when late atrial event sensing is occurring. As described below, late atrial event sensing may be determined when less than a threshold number of the sensed atrial events are sensed during the A3 window and/or within a threshold time interval after the A3 window ending time.

The rate smoothing criteria are applied by control circuit 206 to determine if conditions are met that indicate that the RSI is likely adjusted to an appropriate pacing interval to provide ventricular rate smoothing and avoid a sudden change in ventricular rate. As described below in conjunction with FIG. 9, in some situations the current RSI may be too short or too long, relative to actual paced ventricular cycles, for use in promoting regular ventricular cycle lengths as well as promoting atrial event sensing. When rate smoothing criteria are met, control circuit 206 sets the VV pacing interval to the updated RSI (which may be held at its previously determined value in some instances) at block 612. When the rate smoothing criteria are not met, control circuit 206 sets the VV pacing interval to the post-pace pacing interval determined at block 606.

Figure 9:
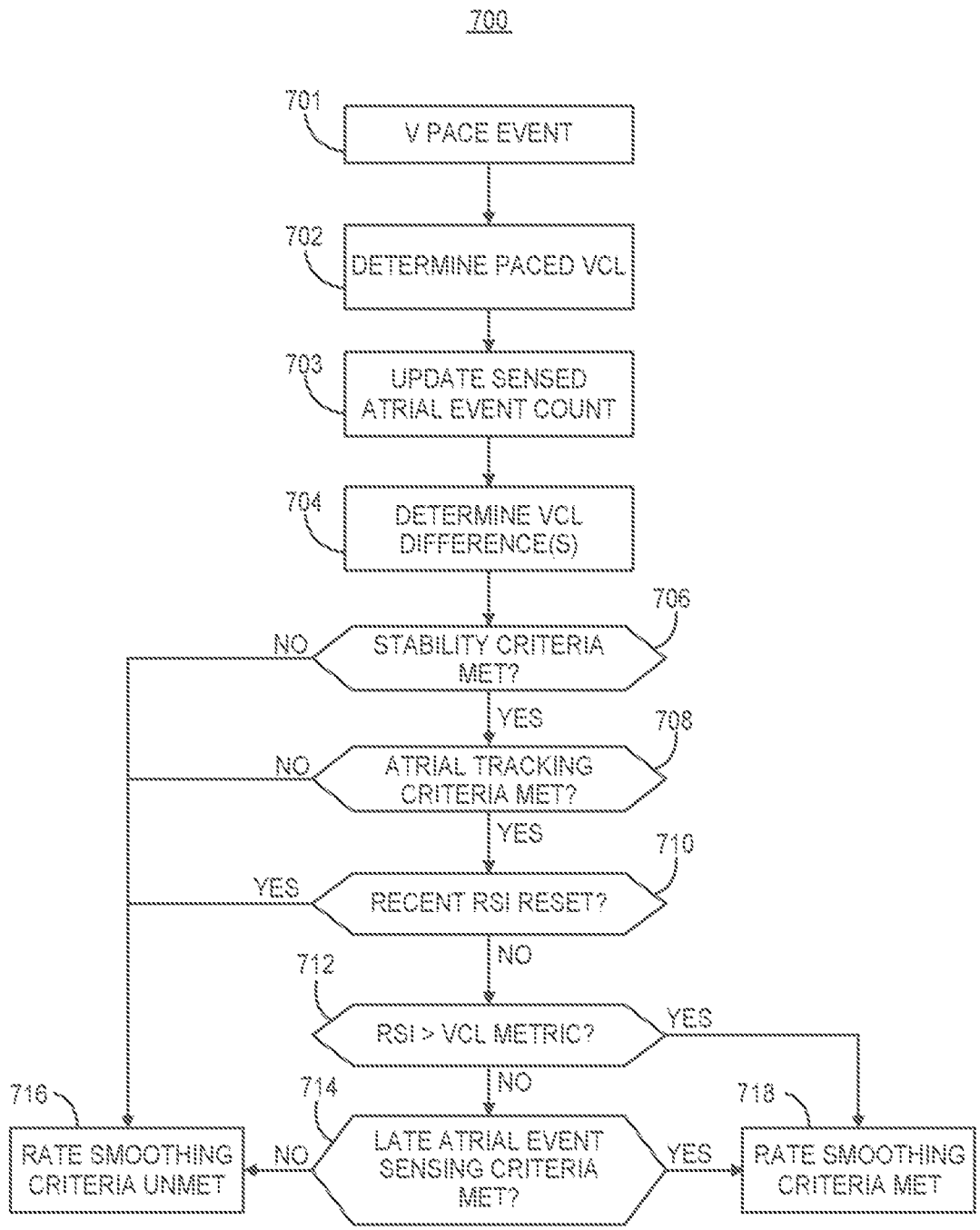
FIG. 9 is a flow chart of a method for determining when rate smoothing criteria are met for controlling VV pacing intervals according to some examples.

FIG. 9 is a flow chart 700 of a method for determining when rate smoothing criteria are met by control circuit 206 according to some examples. The process of flow chart 700 may generally correspond to the determination made at block 610 of FIG. 8 as to whether rate smoothing criteria are met for deciding to set the VV pacing interval following a ventricular pacing pulse to the RSI or to a post-pace pacing interval determined differently than the RSI. In response to each ventricular paced event (block 701), control circuit 206 may determine the paced VCL. The ventricular pacing pulse may be delivered at the expiration of a preceding AV pacing interval or a VV pacing interval, which may be set to the LRI, RSI, post-sense pacing interval or a post-pace pacing interval. The paced VCL is determined as the time interval from the current delivered ventricular pacing pulse to the most recent preceding ventricular event, which may be paced or sensed. The paced VCL may be stored in memory 210 to update the most recent N VCLs stored in memory 210. In some examples, a predetermined number of recent VCLs are stored in memory 210, e.g., in a first-in-first-out basis. The stored VCLs may include Vp-Vp cycle lengths and/or Vs-Vp cycle lengths (and in some examples Vs-Vs and Vp-Vs cycle lengths). The VCLs may be stored for determining whether the ventricular rate is stable (as described below) in order to meet rate smoothing criteria and/or for determining a median VCL, determining an updated value of the RSI and for determining a post-pace pacing interval for use when rate smoothing criteria are not met.

Control circuit 206 may additionally or alternatively update a count of sensed atrial events over a predetermined number of paced ventricular cycles at block 703. The atrial events may be sensed as A4 events in response to the acceleration signal from motion sensor 212 crossing the A4 sensing threshold. In other examples, the atrial events may be P-waves sensed by cardiac electrical signal sensing circuit 204 or correspond to atrial event signals received from another device. In some examples, the atrial events sensed over the N VCLs stored in memory 210 are counted to obtain an atrial sensed event count at block 703. In other examples, the VCLs stored in memory 212 that include a sensed atrial event may be flagged for tracking the atrial event count at block 703. In other examples, the atrial event count may be determined over a different number of ventricular cycles than the N VCLs that may be buffered in memory 210.

At block 704, control circuit 206 may determine VCL differences for use in determining whether the ventricular rate meets stability criteria at block 706. In some examples, only stored VCLs ending on a ventricular pacing pulse are evaluated for determining if the ventricular rate stability criteria are met. In other examples, all VCLs buffered in memory 210, including VCLs ending on a sensed ventricular event may be evaluated. VCLs may be determined to be unstable when the difference between two consecutively determined VCLs is greater than a threshold difference. The difference between each pair of consecutive VCLs may be determined by control circuit 206 at block 706. In other examples, a mean or median VCL may be determined from the N VCLs stored in memory 210 and the difference between each stored VCL and the mean or median VCL may be determined. The greatest difference, the least difference, the sum of differences, the variance or range of the differences or other ventricular rate stability metric may be determined by control circuit 206 based on the VCL differences at block 706. In another example, the difference or range between the longest VCL and the shortest VCL may be determined at the ventricular rate stability metric.

The ventricular rate stability metric may be compared to a stability threshold at block 706. For example, when at least one difference between two of the stored VCLs, which may or may not be consecutive, is greater than a difference threshold, control circuit 206 may determine that the ventricular rate is unstable and that the ventricular rate stability criteria are not met at block 706. In some examples, more than one ventricular rate stability metric may be determined for determining when the stability criteria are met. For example, a metric of VCL differences and a maximum VCL and/or a minimum VCL may all be compared to a respective threshold value for determining when stability criteria are met at block 706.

The rate smoothing criteria may be unmet when the ventricular rate is unstable because the RSI, based on unstable VCLs, may not be adjusted or primed to a pacing interval that avoids an abrupt change in ventricular rate and promotes atrial event sensing. When control circuit 206 determines that the ventricular stability criteria are not met ("no" branch of block 706), control circuit 206 determines that the rate smoothing criteria are unmet at block 716.

As described above in conjunction with FIG. 8, in response to determining that the rate smoothing criteria are unmet, control circuit 206 sets the VV pacing interval started in response to the current delivered ventricular pacing pulse to a post-pace pacing interval (as shown at block 614 of FIG. 8). The post-pace pacing interval may be set to a fixed increment or a percentage greater than the most recently determined paced VCL as described above. In this way, an abrupt change from the preceding paced VCL is avoided and by setting the post-pace pacing interval slightly longer, e.g., 200 ms longer, atrial event sensing during the post-pace pacing interval is promoted, before the next ventricular pacing pulse.

The ventricular rate may be determined to be stable by control circuit 206 at block 706 when VCLs are within a threshold difference of each other and/or other ventricular rate stability metric(s) meet stability criteria at block 706, e.g., according to any of the examples given above. If the ventricular rate is stable based on the stability criteria being met ("yes" branch of block 706), control circuit 206 may determine that rate smoothing criteria are met at block 718. In other examples, as shown in flow chart 700, control circuit 206 may require that one or more additional criteria be satisfied before determining that rate smoothing criteria are met by advancing to block 708.

For instance, control circuit 206 may determine if atrial tracking criteria are met, indicating that ventricular pacing pulses are tracking sensed atrial events, at block 708. In one example, control circuit 206 may compare the sensed atrial event count determined at block 702 to a threshold value. When the sensed atrial event count is equal to the number of ventricular cycles over which the atrial event count was determined, the ventricular pacing pulses are likely tracking sensed atrial events in a 1:1 ratio. In other examples, instead of counting sensed atrial events, control circuit 206 may count the number of ventricular pacing pulses generated in response to the expiration of an AV interval over a predetermined number of VCLs.

When the atrial event count, the number of ventricular pacing pulses delivered at the AV interval following a sensed atrial event, or other metric of atrial synchronized ventricular pacing cycles is less than a threshold value (e.g., out of the most recent N ventricular cycles), control circuit 206 may determine that atrial event tracking criteria are not met at block 708. As examples, if less than four out six, six out of eight, eight out of ten, or ten out of twelve of the most recent ventricular events are ventricular pacing pulses that are delivered at the AV interval from a sensed atrial event, control circuit 206 may determine that atrial event tracking criteria are not met at block 708. In another example, if less than a threshold number or percentage of the N VCLs stored in memory 210 include an atrial sensed event, e.g., less than 70% to 100%, control circuit 206 may determine that atrial tracking criteria are not met at block 708. In some examples, control circuit 206 may determine that atrial event tracking is occurring only when an atrial event is sensed during each ventricular cycle of a predetermined number of consecutive cycles, e.g., three out of three, six out of six, twelve out of twelve, or other predetermined number of ventricular cycles, with a corresponding ventricular pacing pulse delivered at the AV interval for each cycle.

When control circuit 206 determines that atrial tracking criteria are not met at block 708, control circuit 206 may determine that rate smoothing criteria are unmet at block 716. In response to a ventricular pacing pulse and rate smoothing criteria being unmet, control circuit 206 sets the VV pacing interval to the post-pace pacing interval at block 614 of FIG. 8. When atrial synchronous ventricular pacing is not predominate, as determined based on the atrial tracking criteria being unmet, the current RSI may not be appropriately updated for setting the VV pacing interval to the RSI. The RSI may be too long when too few atrial synchronized ventricular pacing pulses have been delivered to cause the RSI to be adjusted to an interval corresponding to a ventricular paced rate that is tracking the atrial rate. As such, the VV pacing interval may be set to the post-pace pacing interval, set based on only the most recent paced VCL in some examples, as described above in conjunction with FIG. 8.

When atrial event tracking criteria are met at block 708, control circuit 206 may determine that the rate smoothing criteria are met (by advancing directly to block 718) and set the VV pacing interval to the RSI (at block 612 of FIG. 8). However, in other examples, as shown in FIG. 9, additional or alternative criteria may be applied by control circuit 206 before determining that the rate smoothing criteria are met, instead of or even when the ventricular rate stability and/or atrial tracking criteria are met. For instance, control circuit 206 may determine if the RSI (or RSBI) has recently been reset, e.g., due to a pacing mode change or other reset condition. The RSI may be reset to the LRI when the pacing mode is switched from a non-atrial tracking ventricular pacing mode, e.g., from a VVI(R) pacing mode, to the atrial tracking pacing mode, e.g., to the VDD pacing mode. The RSBI may be reset to the LRI in response to a pacing mode switch, a programming change of pacing control parameters or other reset conditions in various examples. When the RSBI is reset to the LRI and is adjusted up or down by an adjustment interval based on a comparison to the most recent paced VCL as described above in conjunction with FIG. 6, it may take control circuit 206 several seconds or several minutes to adjust the RSBI to an interval that is equal to or near the current paced VCL. Thus, after a reset, it may take several seconds or minutes for the RSI to be adjusted to an interval that is a rate smoothing increment greater than a VCL corresponding to the actual paced ventricular rate.

Early after a reset of the RSBI to the LRI, therefore, the RSI may not yet be primed to a value that is representative of the atrial synchronized ventricular pacing rate, even when the ventricular pacing pulses are tracking the sensed atrial events and occurring at stable VCLs. Too few atrial synchronized ventricular paced cycles may have occurred since a pacing mode switch, for example, to enable control circuit 206 to adjust the RSBI to the actual paced VCL for use in setting the RSI to an appropriate interval. The RSI may be too long early after a reset compared to actual VCLs, potentially leading to an abrupt change in ventricular rate. As such, in some examples, when the RSI (or RSBI) has been recently reset as determined at block 710, e.g., when the pacing mode has recently switched to the atrial synchronized ventricular pacing mode, control circuit 206 may determine that rate smoothing criteria are unmet at block 716. For instance, when control circuit 206 determines that fewer than a threshold number of VCLs have occurred since a pacing mode switch or programming change, or fewer than a threshold number of ventricular paced cycles have been stored in memory 210 since an RSI reset, control circuit 206 may determine that rate smoothing criteria are unmet at block 716.

In other examples, control circuit 206 may set a timer to a predetermined interval, e.g., to thirty seconds, one minute two minutes or other time interval in response to an RSI reset. Control circuit 206 may determine that a recent RSI reset has occurred at block 710 and that rate smoothing criteria are unmet when the timer is still running and has not expired. Control circuit 206 may set the VV pacing interval to the post-pace pacing interval in response to a ventricular pacing pulse when the recent RSI reset criteria at block 710 are met.

When the RSI has not been recently reset based on criteria applied at block 710, control circuit 206 may advance directly to block 718 and determine that rate smoothing criteria are met. The VV pacing interval may be set to the updated RSI. In some examples, however, before determining that rate smoothing criteria are met, control circuit 206 may additionally or alternatively verify, at block 712, that the currently updated RSI is greater than a VCL metric, e.g., greater than the mean, median or nth longest VCL or other metric determined from VCLs stored in memory 210. The VCL metric may be determined from the most recent 8, 12 (or other predetermined number) of all VCLs, including ventricular cycles ending or starting with a sensed ventricular event, or only VCLs ending with ventricular pacing pulses. If the currently updated RSI is less than or equal to the current VCL metric, the RSI may be too short. A pacing pulse delivered at the RSI may interfere with atrial event sensing. As such, control circuit 206 may determine that rate smoothing criteria are unmet at block 716 in response to the updated RSI being less than or equal to the VCL metric at block 712 ("no" branch). When the RSI is greater than the VCL metric at block 712 ("yes" branch), control circuit 206 may determine that the RSI is appropriate and may advance directly to block 718 to determine that the rate smoothing criteria are met. The VV pacing interval may be set to the RSI.

In other examples, control circuit 206 may additionally or alternatively apply late atrial event sensing criteria as shown in FIG. 9 at block 714 to determine that rate smoothing criteria are met. If atrial events are being sensed predominately late in the ventricular cycle, rate smoothing criteria may be met and the current RSI may be used for appropriate rate smoothing and promoting regular atrial event sensing. However, when sensed atrial events are predominately early in the ventricular cycle, A3 events may be oversensed as A4 events from the motion signal or T-waves may be oversensed as P-waves from the cardiac electrical signal. Using the example of the acceleration signal received from the motion sensor 212, when the atrial event is sensed from the motion signal early in the ventricular cycle, e.g., in the A3 window or within a threshold time interval from the A3 window ending time, an A3 event may be oversensed as the A4 event. When the VV pacing interval is set to the RSI, and the RSI has been adjusted to a relatively short interval, e.g., due to an increasing atrial rate, the A3 window ending time may end early following a ventricular pacing pulse leading to the possibility of oversensing the A3 event as the A4 event, particularly when the atrial rate is slowing again. In this case, the RSI may be too short to promote true atrial event sensing.

As such, control circuit 206 may determine if late atrial event sensing criteria are met at block 714. A late atrial event count may be determined as the number of atrial events sensed after a threshold time interval from a ventricular event out of the updated sensed atrial event count, for example. A sensed atrial event may be counted as a late atrial event when the atrial event is sensed later than the A3 window ending time or later than a threshold time interval after the A3 window ending time, e.g., 50 to 100 ms after the A3 window ending time. In another example, early atrial events may be identified and counted as atrial events that are sensed before a threshold time interval after a ventricular event, e.g., before a threshold time interval after the A3 window ending time. When an early atrial event count (e.g., the number of atrial events counted at block 702 that are sensed before the threshold time interval after the A3 window ending time) is greater than or equal to a threshold, late atrial event sensing criteria may be unmet at block 714. In some examples, a single early atrial event may result in control circuit 206 determining that late atrial event sensing criteria are unmet, and rate smoothing criteria are unmet at block 718. In other examples, a threshold number of 2, 3, 4, 5, 8 or other consecutive or non-consecutive number of early atrial events, e.g., during the A3 window or within 50 to 100 ms of the A3 window ending time, may be required to determine that the late atrial event sensing criteria are unmet. The threshold number may be defined as a ratio or percentage of a predetermined number of ventricular cycles or sensed atrial events. For example, when at least 3 out of 5, 4 out of 5, or 5 out of 5 sensed atrial events are early atrial events, control circuit 206 may determine that the late atrial event sensing criteria are unmet at bock 714. Conversely, the late atrial event sensing criteria at block 714 may be met when a threshold number of atrial events out of all sensed atrial events be identified as late atrial events, sensed after the threshold time interval after a ventricular event, e.g., 50 ms after the A3 window ending time.

Control circuit 206 determines that rate smoothing criteria are unmet at block 716 in response to the late atrial event criteria being unmet at block 714 and sets the VV pacing interval to the post-pace pacing interval (block 614 of FIG. 8). In this situation, when early atrial event sensing is occurring, the RSI may be shorter than appropriate since ventricular pacing may be tracking oversensed A3 events or premature atrial contractions. The RSI may have been progressively shortened due to relatively short paced VCLs that tracked an increasing ventricular pacing rate. In order to avoid pacing at a shortened RSI that may interfere with true atrial event sensing, particularly as the atrial rate slows, the VV pacing interval may be set to the relatively longer post-pace pacing interval, set to the most recent paced VCL plus an increment, in response to a ventricular pacing pulse when late atrial event sensing criteria are unmet, particularly when the RSI is less than or equal to the VCL metric ("no" branch of block 712). The late atrial event sensing criteria may require that at least a threshold number of atrial events (early and late combined) are sensed over a predetermined number of VCLs in order to determine that late atrial event sensing criteria are met.

However, when the late atrial event sensing criteria are met at block 714, e.g., when the early atrial event count is less than a predetermined threshold at block 714 (or the late atrial event count is greater than a predetermined threshold), control circuit 206 determines that the rate smoothing criteria are met at block 718. The VV pacing interval is set to the RSI (at block 612 of FIG. 8). Even though the RSI may be relatively short, e.g., less than or equal to the median VCL or another VCL metric, proper tracking of sensed atrial events that are sensed relatively late in the ventricular cycle is likely. Control circuit 206 may set the VV pacing interval to the RSI (block 612 of FIG. 8) in response to the rate smoothing criteria being met at block 718.

In the example of FIG. 9, multiple criteria are shown to be included in determining whether rate smoothing criteria are met or not, e.g., rate stability criteria (block 706), atrial tracking criteria (block 708), recent RSI reset criteria (block 710), RSI being greater than a VCL metric (block 712), and late atrial event sensing criteria (block 714). It is to be understood that in other examples, any one or more of these criteria may be applied in any combination for determining whether the rate smoothing criteria are met. Two or more of the criteria described in conjunction with decision blocks 706 through 714 may be applied according to one or more combinations of Boolean operations, e.g., in logical AND and/or logical OR and/or NOT combinations in various examples. For example, control circuit 206 may determine that rate smoothing criteria are met when one of the rate stability criteria and atrial tracking criteria are met but not the recent RSI reset criteria. Additionally or alternatively, control circuit 206 may determine that rate smoothing criteria are met when the atrial tracking criteria are met and the late atrial event sensing criteria are met. The various examples of rate smoothing criteria described above may be applied alone or together in any combination and are not limited to the specific combinations described above and intended as illustrative examples without limitation.

In an atrial synchronous ventricular pacing system in which atrial event signals may have a relatively low or variable amplitude and variable timing relative to ventricular events, applying an RSI following a ventricular pacing pulse promotes recovery of atrial event sensing, e.g., when atrial event undersensing is occurring, while supporting a regular ventricular rate. However, when conditions exist that indicate that the RSI may not be primed for appropriate rate smoothing, e.g., too long or too short for promoting atrial event sensing and regular ventricular cycle lengths, the VV pacing interval may be set to a temporary post-pace pacing interval to provide rate smoothing that is set based on the most recent paced VCL, to promote ventricular cycle length regularity and atrial event sensing to regain tracking until the RSI is adjusted to an appropriate interval.

Furthermore, as described above, setting a post-sense pacing interval, which may be shorter than the LRI, following intrinsic ventricular sensed events may avoid a short-long interval sequence associated with PVCs, which can lead to arrhythmias in some instances. The post-sense pacing interval promotes sensing of the atrial event during the next ventricular cycle by being set, at least in some examples, to the most recent VCL plus a relatively larger increment than the increment used to set the RSI while still avoiding a ventricular cycle length that is much longer than the VCL ending on a sensed R-wave.

The rate smoothing techniques disclosed herein may be implemented in a variety of ventricular pacing systems and are useful in ventricular pacing systems that include a sensor, such as a motion sensor or electrodes, for sensing atrial events from a signal that is acquired from a ventricular location, e.g., in or on the ventricles. The far-field atrial event signals in a cardiac signal acquired from a ventricular location (or more generally a non-atrial location) may be oversensed or undersensed during atrial synchronous ventricular pacing. The rate smoothing techniques disclosed herein may be useful in ventricular pacing systems that receive an atrial event signal from another medical device when the ventricular pacemaker is implanted in a ventricular location, e.g., in or on the ventricles. The techniques disclosed herein for setting VV pacing intervals promote restoring atrial event sensing under a variety of circumstances and promote stable VCLs during possible conditions of both undersensing and oversensing of atrial event signals.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A pacemaker comprising:
a pulse generator configured to generate ventricular pacing pulses;
a cardiac electrical signal sensing circuit configured to sense ventricular event signals;
a control circuit configured to:
determine a first ventricular cycle length ending with a first ventricular pacing pulse of the ventricular pacing pulses generated by the pulse generator;
determine a rate smoothing pacing interval based on at least the first ventricular cycle length;
determine a second ventricular cycle length ending with a ventricular event signal sensed by the cardiac electrical signal sensing circuit;
determine a post-sense ventricular pacing interval based on the second ventricular cycle length;
start a ventricular pacing interval set to the post-sense ventricular pacing interval in response to the ventricular event signal sensed by the cardiac electrical signal sensing circuit; and determine that the post-sense ventricular pacing interval expires;

wherein the pulse generator is configured to generate a second ventricular pacing pulse in response to the control circuit determining the expiration of the post-sense ventricular pacing interval; and the control circuit is further configured to:
start the ventricular pacing interval set to the rate smoothing pacing interval in response to the pulse generator generating the second ventricular pacing pulse at the expiration of the post-sense ventricular pacing interval;
update the first ventricular cycle length in response to each ventricular pacing pulse that is generated by the pulse generator at an expiration of one of an atrioventricular pacing interval or the rate smoothing pacing interval;
update the rate smoothing pacing interval in response to the updated first ventricular cycle length; and
withhold updating the rate smoothing pacing interval in response to the second ventricular pacing pulse generated by the pulse generator at the expiration of the post-sense ventricular pacing interval.

2. The medical device of claim 1, wherein the control circuit is further configured to:
receive an atrial event signal;
set the atrioventricular pacing interval in response to the received atrial event signal; and
determine that the atrioventricular pacing interval expires;
wherein the pulse generator is configured to generate the first ventricular pacing pulse in response to the atrioventricular pacing interval expiring; and
wherein the control circuit is configured to determine the first ventricular cycle length ending with the first ventricular pacing pulse generated in response to the atrioventricular pacing interval expiring.

3. The medical device of claim 2, further comprising a sensor configured to sense a cardiac signal;
wherein the control circuit is configured to receive the atrial event signal by:
receiving the cardiac signal from the sensor; and
sensing the atrial event signal from the cardiac signal.

4. The medical device of claim 3, wherein the sensor comprises any of: an electrode, an accelerometer, an acoustical sensor an impedance sensor and a pressure sensor.

5. The medical device of claim 2, further comprising a communication circuit,
wherein the control circuit is configured to receive, via the communication circuit, the atrial event signal transmitted from another medical device.

6. The medical device of claim 1, wherein the control circuit is further configured to determine the post-sense ventricular pacing interval based on the second ventricular cycle length by determining a greater one of the second ventricular cycle length plus an increment and a predetermined minimum post-sense ventricular pacing interval.

7. The medical device of claim 1, wherein the control circuit is further configured to determine the post-sense ventricular pacing interval by:
determining that the second ventricular cycle length plus an increment is greater than a maximum limit; and
determining the post-sense ventricular pacing interval to be the maximum limit in response to the second ventricular cycle length plus the increment being greater than the maximum limit.

8. The medical device of claim 1, wherein the control circuit is further configured to set the ventricular pacing interval to the rate smoothing pacing interval by:
determining a first pacing interval based on at least the first ventricular cycle length according to a first method;
determining a second pacing interval based on the first ventricular cycle length according to a second method different than the first method;
determining when rate smoothing criteria are met;
setting the ventricular pacing interval to the first pacing interval in response to the rate smoothing criteria being met; and
setting the ventricular pacing interval to the second pacing interval in response to the rate smoothing criteria not being met.

9. The medical device of claim 8, wherein the control circuit is configured to determine that the rate smoothing criteria are met by:
determining a ventricular cycle length metric from a plurality of preceding ventricular cycle lengths; and
determining that the first pacing interval is greater than the ventricular cycle length metric.

10. The medical device of claim 8, wherein the control circuit is further configured to:
reset the rate smoothing interval to an initial value; and
determine that the rate smoothing criteria are met by determining that at least a threshold number of ventricular cycles have occurred since resetting the rate smoothing interval.

11. The medical device of claim 8, further comprising a sensor for sensing a cardiac signal,
wherein the control circuit is further configured to:
sense atrial events from the cardiac signal; and
determine that the rate smoothing criteria are met by determining that atrial tracking criteria are met based on at least a threshold number of atrial events being sensed from the cardiac signal.

12. The medical device of claim 8, wherein the control circuit is further configured to determine that the rate smoothing criteria are met by determining that a plurality of ventricular cycle lengths meet rate stability criteria.

13. The medical device of claim 8, further comprising a sensor sensing a cardiac signal;
wherein the control circuit is further configured to:
sense an atrial event from the cardiac signal;
determine that the atrial event is sensed after a threshold time interval following a preceding ventricular event; and
determine that the rate smoothing criteria are met in response to determining that the atrial event is sensed after the threshold time interval.

14. A non-transitory, computer-readable storage medium comprising a set of instructions which, when executed by a control circuit of a medical device, cause the medical device to:
generate a first ventricular pacing pulse;
determine a first ventricular cycle length ending with the first ventricular pacing pulse;
determine a rate smoothing pacing interval based on at least the first ventricular cycle length;
sense a ventricular event signal from a cardiac electrical signal;
determine a second ventricular cycle length ending with the sensed ventricular event signal;
determine a post-sense ventricular pacing interval based on the second ventricular cycle length;

start a ventricular pacing interval set to the post-sense ventricular pacing interval in response to the sensed ventricular event signal;

determine that the post-sense ventricular pacing interval expires;

generate a second ventricular pacing pulse in response to the expiration of the post-sense ventricular pacing interval;

start the ventricular pacing interval set to the rate smoothing pacing interval in response to the second ventricular pacing pulse generated at the expiration of the post-sense ventricular pacing interval;

update the first ventricular cycle length in response to each ventricular pacing pulse that is generated at an expiration of one of an atrioventricular pacing interval or the rate smoothing interval;

update the rate smoothing pacing interval in response to the updated first ventricular cycle length; and withhold updating the rate smoothing pacing interval in response to the second ventricular pacing pulse at the expiration of the post-sense ventricular pacing interval.

15. The non-transitory, computer-readable storage medium of claim 14 further comprising instructions that cause the medical device to:

receive an atrial event signal;

set the atrioventricular pacing interval in response to receiving the atrial event signal;

determine that the atrioventricular pacing interval expires;

generate the first ventricular pacing pulse in response to the atrioventricular pacing interval expiring; and determine the first ventricular cycle length ending with the first ventricular pacing pulse generated in response to the atrioventricular pacing interval expiring.

16. The non-transitory, computer-readable storage medium of claim 15 further comprising instructions that cause the medical device to receive the atrial event signal by:

sensing a cardiac signal by a sensor; and sensing the atrial event signal from the cardiac signal.

17. The non-transitory, computer-readable storage medium of claim 16 further comprising instructions that cause the medical device to sense the cardiac signal by sensing any of a cardiac electrical signal, an acceleration signal, an acoustical signal, an impedance signal and a pressure signal.

18. The non-transitory, computer-readable storage medium of claim 15 further comprising instructions that cause the medical device to receive the atrial event signal by receiving the atrial event signal transmitted from another medical device.

19. The non-transitory, computer-readable storage medium of claim 14 further comprising instructions that cause the medical device to determine the post-sense ventricular pacing interval based on the second ventricular cycle length by determining a greater one of the second ventricular cycle length plus an increment and a predetermined minimum post-sense ventricular pacing interval.

* * * * *